US007476654B2

(12) United States Patent
Alitalo et al.

(10) Patent No.: US 7,476,654 B2
(45) Date of Patent: Jan. 13, 2009

(54) METHOD FOR MODULATING, REGULATING AND/OR STABILIZING ANGIOGENESIS

(75) Inventors: Kari Alitalo, Helsinki (FI); Ulf Eriksson, Stockholm (SE); Marko Uutela, Helsinki (FI)

(73) Assignee: Ludwig Institute for Cancer Research, New York, NY (US)

( * ) Notice: Subject to any disclaimer, the term of this patent is extended or adjusted under 35 U.S.C. 154(b) by 82 days.

(21) Appl. No.: 11/073,605

(22) Filed: Mar. 8, 2005

(65) Prior Publication Data

US 2005/0260161 A1    Nov. 24, 2005

Related U.S. Application Data

(60) Provisional application No. 60/550,327, filed on Mar. 8, 2004.

(51) Int. Cl.
*A61K 38/18* (2006.01)
(52) U.S. Cl. ............................ 514/12; 530/350; 530/399
(58) Field of Classification Search ........................ None
See application file for complete search history.

(56) References Cited

FOREIGN PATENT DOCUMENTS

| WO | WO 00/27879 | * | 5/2000 |
| WO | WO 01/62942 A2 | * | 8/2001 |

OTHER PUBLICATIONS

Judah Folkman, et al., "Angiogenesis", The Journal of Biological Chemistry, (Jun. 5, 1992), pp. 10931-10934, vol. 267, No. 16, The American Society for Biochemistry and Molecular Biology, Inc.
B. Olofsson, et al., "A Novel Vascular Endothelial Growth Factor, VEGF-C, is a Ligand for the Flt4 (VEGFR-3) and KDR (VEGFR-2) Receptor Tyrosine Kinases", The EMBO Journal, (1986), pp. 290-298, vol. 15, No. 2, Oxford University Press.
Hans Bostroem, et al., "PDGF-A Signaling is a Critical Event in Lung Alveolar Myofibroblast Development and Alveogensis", Cell, (Jun. 14, 1996), pp. 863-873, vol. 85, Cell Press 1997.
Per Lindahl, et al., "Pericyte Loss and Microaneurysm Formation in PDGF-B-Deficient Mice", Science, (Jul. 11, 1997), pp. 242-245, vol. 277.
Per Lindahl, et al., "Paracine PDGF-B/PDGF-Rβ Signaling Controls Mesangial Cell Development In Kidney Glomeruil", Development, (1998), pp. 3313-3322, vol. 125, Printed in Great Britain, The Company of Biologists Limited.
Zoya Poltorak, et al., "$VEGF_{145}$, a Secreted Vascular Endothelial Growth Factor Isoform That Binds to Extracellular Matrix", The Journal of Biological Chemistry, (Mar. 14, 1997), pp. 7151-7158, vol. 272, No. 11, The American Society for Biochemistry and Molecular Biology, Inc.
Steven Hopkins, et al., "Controlled Delivery of Vascular Endothelial Growth Factor Promotes Neovascularization and Maintains Limb Function in a Rabbit Model of Ischemia", Journal of Vascular Surgery, pp. 886-895, vol. 27, No. 5.
Iris Baumgartner, MD, "Constitutive Expression of ph $VEGF_{165}$ After Intramuscular Gene Transfer Promotes Collateral Vessel Development in Patients with Critical Lamb Ischemia". Clinical Investigation and Reports, Circulation, (1998) pp. 1114-1123, No. 97.
Anders Kvanta, et al., "Subfoveal Fibrovascular Membranes in Age-Related Mascular Degeneration Express Vascular Endothelial Growth Factor", Investigative Ophthalmology & Visual Science, (Aug. 1996), vol. 37, No. 9.

* cited by examiner

*Primary Examiner*—Marianne P Allen
(74) *Attorney, Agent, or Firm*—Fulbright & Jaworski LLP

(57) ABSTRACT

A method of modulating, regulating and/or stabilizing angiogenesis in a mammal in need thereof, in which the PDGF-D level or activity or both in the mammal are modulated or increased. In preferred embodiments, an active PDGF-D polypeptide, or a polynucleotide encoding an active PDGF-D is administered to the mammal, preferably at a location where angiogenesis modulation or stabilization is desired. The PDGF-D is advantageously co-administered with an angiogenic growth factor, such as a member of the VEGF family of growth factors, in particular VEGF-E. The claimed method inhibits leakage of blood vessels and is useful, inter alia, for treatment of edemas.

6 Claims, 18 Drawing Sheets

Met His Arg Leu Ile Phe Val Tyr Thr Leu Ile Cys Ala Asn Phe
1               5               10              15

Cys Ser Cys Arg Asp Thr Ser Ala Thr Pro Gln Ser Ala Ser Ile Lys
            20              25              30

Ala Leu Arg Asn Ala Asn Leu Arg Arg Asp Glu Ser Asn His Leu Thr
            35              40              45

Asp Leu Tyr Arg Arg Asp Glu Thr Ile Gln Val Lys Gly Asn Gly Tyr
        50              55              60

Val Gln Ser Pro Arg Phe Pro Asn Ser Tyr Pro Arg Asn Leu Leu Leu
    65              70              75

Thr Trp Arg Leu His Ser Gln Glu Asn Thr Arg Ile Gln Leu Val Phe
80              85              90              95

Asp Asn Gln Phe Gly Leu Glu Glu Ala Glu Asn Asp Ile Cys Arg Tyr
            100             105             110

Asp Phe Val Glu Val Glu Asp Ile Ser Glu Thr Ser Thr Ile Ile Arg
            115             120             125

Gly Arg Trp Cys Gly His Lys Glu Val Pro Pro Arg Ile Lys Ser Arg
            130             135             140

Thr Asn Gln Ile Lys Ile Thr Phe Lys Ser Asp Asp Tyr Phe Val Ala
    145             150             155

Lys Pro Gly Phe Lys Ile Tyr Tyr Ser Leu Leu Glu Asp Phe Gln Pro
160             165             170             175

Ala Ala Ala Ser Glu Thr Asn Trp Glu Ser Val Thr Ser Ser Ile Ser
            180             185             190

Gly Val Ser Tyr Asn Ser Pro Ser Val Thr Asp Pro Thr Leu Ile Ala
        195             200             205

Asp Ala Leu Asp Lys Lys Ile Ala Glu Phe Asp Thr Val Glu Asp Leu
        210             215             220

Leu Lys Tyr Phe Asn Pro Glu Ser Trp Gln Glu Asp Leu Glu Asn Met
    225             230             235

```
Tyr Leu Asp Thr Pro Arg Tyr Arg Gly Arg Ser Tyr His Asp Arg Lys
240             245             250             255

Ser Lys Val Asp Leu Asp Arg Leu Asn Asp Asp Ala Lys Arg Tyr Ser
            260             265             270

Cys Thr Pro Arg Asn Tyr Ser Val Asn Ile Arg Glu Glu Leu Lys Leu
            275             280             285

Ala Asn Val Val Phe Phe Pro Arg Cys Leu Leu Val Gln Arg Cys Gly
        290             295             300

Gly Asn Cys Gly Cys Gly Thr Val Asn Trp Arg Ser Cys Thr Cys Asn
    305             310             315

Ser Gly Lys Thr Val Lys Lys Tyr His Glu Val Leu Gln Phe Glu Pro
320             325             330             335

Gly His Ile Lys Arg Arg Gly Arg Ala Lys Thr Met Ala Leu Val Asp
            340             345             350

Ile Gln Leu Asp His His Glu Arg Cys Asp Cys Ile Cys Ser Ser Arg
            355             360             365

Pro Pro Arg
        370
```

```
cgctcggaaa gttcagcatg caggaagttt ggggagagct cggcgattag cacagcgacc   60
cgggccagcg cagggcgagc gcaggcggcg agagcgcagg gcggcgcggc gtcggtcccg  120
ggagcagaac ccggcttttt cttggagcga cgctgtctct agtcgctgat cccaa       175
```

| atg | cac | cgg | ctc | atc | ttt | gtc | tac | act | cta | atc | tgc | gca | aac | ttt | tgc | 223 |
|---|---|---|---|---|---|---|---|---|---|---|---|---|---|---|---|---|
| Met | His | Arg | Leu | Ile | Phe | Val | Tyr | Thr | Leu | Ile | Cys | Ala | Asn | Phe | Cys | |
| 1 | | | | 5 | | | | | 10 | | | | | 15 | | |

| agc | tgt | cgg | gac | act | tct | gca | acc | ccg | cag | agc | gca | tcc | atc | aaa | gct | 271 |
|---|---|---|---|---|---|---|---|---|---|---|---|---|---|---|---|---|
| Ser | Cys | Arg | Asp | Thr | Ser | Ala | Thr | Pro | Gln | Ser | Ala | Ser | Ile | Lys | Ala | |
| | | | 20 | | | | | 25 | | | | | 30 | | | |

| ttg | cgc | aac | gcc | aac | ctc | agg | cga | gat | gag | agc | aat | cac | ctc | aca | gac | 319 |
|---|---|---|---|---|---|---|---|---|---|---|---|---|---|---|---|---|
| Leu | Arg | Asn | Ala | Asn | Leu | Arg | Arg | Asp | Glu | Ser | Asn | His | Leu | Thr | Asp | |
| | | 35 | | | | | 40 | | | | | 45 | | | | |

| ttg | tac | cga | aga | gat | gag | acc | atc | cag | gtg | aaa | gga | aac | ggc | tac | gtg | 367 |
|---|---|---|---|---|---|---|---|---|---|---|---|---|---|---|---|---|
| Leu | Tyr | Arg | Arg | Asp | Glu | Thr | Ile | Gln | Val | Lys | Gly | Asn | Gly | Tyr | Val | |
| | 50 | | | | | 55 | | | | | 60 | | | | | |

| cag | agt | cct | aga | ttc | ccg | aac | agc | tac | ccc | agg | aac | ctg | ctc | ctg | aca | 415 |
|---|---|---|---|---|---|---|---|---|---|---|---|---|---|---|---|---|
| Gln | Ser | Pro | Arg | Phe | Pro | Asn | Ser | Tyr | Pro | Arg | Asn | Leu | Leu | Leu | Thr | |
| 65 | | | | | 70 | | | | | 75 | | | | | 80 | |

| tgg | cgg | ctt | cac | tct | cag | gag | aat | aca | cgg | ata | cag | cta | gtg | ttt | gac | 463 |
|---|---|---|---|---|---|---|---|---|---|---|---|---|---|---|---|---|
| Trp | Arg | Leu | His | Ser | Gln | Glu | Asn | Thr | Arg | Ile | Gln | Leu | Val | Phe | Asp | |
| | | | | 85 | | | | | 90 | | | | | 95 | | |

| aat | cag | ttt | gga | tta | gag | gaa | gca | gaa | aat | gat | atc | tgt | agg | tat | gat | 511 |
|---|---|---|---|---|---|---|---|---|---|---|---|---|---|---|---|---|
| Asn | Gln | Phe | Gly | Leu | Glu | Glu | Ala | Glu | Asn | Asp | Ile | Cys | Arg | Tyr | Asp | |
| | | | 100 | | | | | 105 | | | | | 110 | | | |

| ttt | gtg | gaa | gtt | gaa | gat | ata | tcc | gaa | acc | agt | acc | att | att | aga | gga | 559 |
|---|---|---|---|---|---|---|---|---|---|---|---|---|---|---|---|---|
| Phe | Val | Glu | Val | Glu | Asp | Ile | Ser | Glu | Thr | Ser | Thr | Ile | Ile | Arg | Gly | |
| | | 115 | | | | | 120 | | | | | 125 | | | | |

| cga | tgg | tgt | gga | cac | aag | gaa | gtt | cct | cca | agg | ata | aaa | tca | aga | acg | 607 |
|---|---|---|---|---|---|---|---|---|---|---|---|---|---|---|---|---|
| Arg | Trp | Cys | Gly | His | Lys | Glu | Val | Pro | Pro | Arg | Ile | Lys | Ser | Arg | Thr | |
| | 130 | | | | | 135 | | | | | 140 | | | | | |

| aac | caa | att | aaa | atc | aca | ttc | aag | tcc | gat | gac | tac | ttt | gtg | gct | aaa | 655 |
|---|---|---|---|---|---|---|---|---|---|---|---|---|---|---|---|---|
| Asn | Gln | Ile | Lys | Ile | Thr | Phe | Lys | Ser | Asp | Asp | Tyr | Phe | Val | Ala | Lys | |
| 145 | | | | 150 | | | | | 155 | | | | | 160 | | |

```
cct gga ttc aag att tat tat tct ttg ctg gaa gat ttc caa ccc gca        703
Pro Gly Phe Lys Ile Tyr Tyr Ser Leu Leu Glu Asp Phe Gln Pro Ala
            165             170             175 gca gct tca gag acc aac tgg gaa tct gtc aca agc tct att tca ggg        751
Ala Ala Ser Glu Thr Asn Trp Glu Ser Val Thr Ser Ser Ile Ser Gly
        180             185             190 gta tcc tat aac tct cca tca gta acg gat ccc act ctg att gcg gat        799
Val Ser Tyr Asn Ser Pro Ser Val Thr Asp Pro Thr Leu Ile Ala Asp
        195             200             205 gct ctg gac aaa aaa att gca gaa ttt gat aca gtg gaa gat ctg ctc        847
Ala Leu Asp Lys Lys Ile Ala Glu Phe Asp Thr Val Glu Asp Leu Leu
        210             215             220 aag tac ttc aat cca gag tca tgg caa gaa gat ctt gag aat atg tat        895
Lys Tyr Phe Asn Pro Glu Ser Trp Gln Glu Asp Leu Glu Asn Met Tyr
225             230             235             240 ctg gac acc cct cgg tat cga ggc agg tca tac cat gac cgg aag tca        943
Leu Asp Thr Pro Arg Tyr Arg Gly Arg Ser Tyr His Asp Arg Lys Ser
            245             250             255 aaa gtt gac ctg gat agg ctc aat gat gat gcc aag cgt tac agt tgc        991
Lys Val Asp Leu Asp Arg Leu Asn Asp Asp Ala Lys Arg Tyr Ser Cys
        260             265             270 act ccc agg aat tac tcg gtc aat ata aga gaa gag ctg aag ttg gcc       1039
Thr Pro Arg Asn Tyr Ser Val Asn Ile Arg Glu Glu Leu Lys Leu Ala
        275             280             285 aat gtg gtc ttc ttt cca cgt tgc ctc ctc gtg cag cgc tgt gga gga       1087
Asn Val Val Phe Phe Pro Arg Cys Leu Leu Val Gln Arg Cys Gly Gly
        290             295             300 aat tgt ggc tgt gga act gtc aac tgg agg tcc tgc aca tgc aat tca       1135
Asn Cys Gly Cys Gly Thr Val Asn Trp Arg Ser Cys Thr Cys Asn Ser
305             310             315             320 ggg aaa acc gtg aaa aag tat cat gag gta tta cag ttt gag cct ggc       1183
Gly Lys Thr Val Lys Lys Tyr His Glu Val Leu Gln Phe Glu Pro Gly
            325             330             335
```

Fig. 2 (cont.)

```
cac atc aag agg agg ggt aga gct aag acc atg gct cta gtt gac atc    1231
His Ile Lys Arg Arg Gly Arg Ala Lys Thr Met Ala Leu Val Asp Ile
            340             345             350 cag ttg gat cac cat gaa cga tgc gat tgt atc tgc agc tca aga cca    1279
Gln Leu Asp His His Glu Arg Cys Asp Cys Ile Cys Ser Ser Arg Pro
            355             360             365 cct cga taagagaatg tgcacatcct tacattaagc ctgaaagaac ctttagttta     1335
Pro Arg
    370 aggagggtga gataagagac ccttttccta ccagcaacca aacttactac tagcctgcaa  1395
tgcaatgaac acaagtggtt gctgagtctc agccttgctt tgttaatgcc atggcaagta  1455
gaaaggtata tcatcaactt ctatacctaa gaatatagga ttgcatttaa taatagtgtt  1515
tgaggttata tatgcacaaa cacacacaga aatatattca tgtctatgtg tatatagatc  1575
aaatgttttt tttggtatat ataaccaggt acaccagagc ttacatatgt ttgagttaga  1635
ctcttaaaat cctttgccaa aataagggat ggtcaaatat atgaaacatg tctttagaaa  1695
atttaggaga taaatttatt tttaaatttt gaaacacaaa acaatttga atcttgctct   1755
cttaaagaaa gcatcttgta tattaaaaat caaaagatga ggctttctta catatacatc  1815
ttagttgatt attaaaaaag gaaaaggtt tccagagaaa aggccaatac ctaagcattt   1875
tttccatgag aagcactgca tacttaccta tgtggactgt aataacctgt ctccaaaacc  1935
atgccataat aatataagtg ctttagaaat taaatcattg tgtttttat gcatttgct    1995
gaggcatcct tattcattta acacctatct caaaaactta cttagaaggt ttttattat   2055
agtcctacaa aagacaatgt ataagctgta acagaatttt gaattgtttt tctttgcaaa  2115
acccctccac aaaagcaaat cctttcaaga atggcatggg cattctgtat gaacctttcc  2175
agatggtgtt cagtgaaaga tgtgggtagt tgagaactta aaaagtgaac attgaaacat  2235
cgacgtaact ggaaaccg                                                2253
```

Gly Arg Phe Pro Thr Arg Ser Ser Phe Arg Asp Gln Leu Glu Ser Val
 1           5               10              15

Thr Ser Ser Val Ser Gly Tyr Pro Tyr Asn Ser Pro Ser Val Thr Asp
            20              25              30

Pro Thr Leu Ile Ala Asp Ala Leu Asp Lys Lys Ile Ala Glu Phe Asp
        35              40              45

Thr Val Glu Asp Leu Leu Lys Tyr Phe Asn Pro Glu Ser Trp Gln Glu
        50              55              60

Asp Leu Glu Asn Met Tyr Leu Asp Thr Pro Arg Tyr Arg Gly Arg Ser
 65              70              75              80

Tyr His Asp Arg Lys Ser Lys Val Asp Leu Asp Arg Leu Asn Asp Asp
            85              90              95

Ala Lys Arg Tyr Ser Cys Thr Pro Arg Asn Tyr Ser Val Asn Ile Arg
            100             105             110

Glu Glu Leu Lys Leu Ala Asn Val Val Phe Phe Pro Arg Cys Leu Leu
        115             120             125

Val Gln Arg Cys Gly Gly Asn Cys Gly Cys Gly Thr Val Lys Leu Glu
        130             135             140

Ser Cys Thr Cys Asn Ser Gly Lys Thr Val Lys Lys Tyr His Glu Val
145             150             155             160

Leu Gln Phe Glu Pro Gly His Ile Lys Arg Arg Gly Arg Ala Lys Thr
            165             170             175

Met Ala Leu Val Asp Ile Gln Leu Asp His His Glu Arg Cys Asp Cys
            180             185             190

Ile Cys Ser Ser Arg Pro Pro Arg
        195             200

```
Leu Tyr Arg Arg Asp Glu Thr Ile Gln Val Lys Gly Asn Gly Tyr Val
 1           5              10                  15
Gln Ser Pro Arg Phe Pro Asn Ser Tyr Pro Arg Asn Leu Leu Leu Thr
            20              25              30
Trp Arg Leu His Ser Gln Glu Asn Thr Arg Ile Gln Leu Val Phe Asp
        35              40              45
Asn Gln Phe Gly Leu Glu Glu Ala Glu Asn Asp Ile Cys Arg Tyr Asp
    50              55              60
Phe Val Glu Val Glu Asp Ile Ser Glu Thr Ser Thr Ile Ile Arg Gly
 65             70              75              80
Arg Trp Cys Gly His Lys Glu Val Pro Pro Arg Ile Lys Ser Arg Thr
                85              90              95
Asn Gln Ile Lys Ile Thr Phe Lys Ser Asp Asp Tyr Phe Val Ala Lys
            100             105             110
Pro Gly Phe Lys Ile Tyr Tyr Ser Leu Leu Glu Asp Phe Gln Pro Ala
            115             120             125
Ala Ala Ser Glu Thr Asn Trp Glu Ser Val Thr Ser Ser Ile Ser Gly
        130             135             140
Val Ser Tyr Asn Ser Pro Ser Val Thr Asp Pro Thr Leu Ile Ala Asp
145             150             155             160
Ala Leu Asp Lys Lys Ile Ala Glu Phe Asp Thr Val Glu Asp Leu Leu
            165             170             175
Lys Tyr Phe Asn Pro Glu Ser Trp Gln Glu Asp Leu Glu Asn Met Tyr
            180             185             190
Leu Asp Thr Pro Arg Tyr Arg Gly Arg Ser Tyr His Asp Arg Lys Ser
        195             200             205
Lys Val Asp Leu Asp Arg Leu Asn Asp Asp Ala Lys Arg Tyr Ser Cys
210             215             220
Thr Pro Arg Asn Tyr Ser Val Asn Ile Arg Glu Glu Leu Lys Leu Ala
225             230             235             240
Asn Val Val Phe Phe Pro Arg Cys Leu Leu Val Gln Arg Cys Gly Gly
            245             250             255
Asn Cys Gly Cys Gly Thr Val Asn Trp Arg Ser Cys Thr Cys Asn Ser
            260             265             270
Gly Lys Thr Val Lys Lys Tyr His Glu Val Leu Gln Phe Glu Pro Gly
        275             280             285
His Ile Lys Arg Arg Gly Arg Ala Lys Thr Met Ala Leu Val Asp Ile
        290             295             300
Gln Leu Asp His His Glu Arg Cys Asp Cys Ile Cys Ser Ser Arg Pro
305             310             315             320
Pro Arg
```

```
PDGF-D   MHRLIFVYTLICANFCSCRQTSATPQSSASIKALRHANLRR      40
PDGF-C   MSLFGLLLVTSALAGQRRGTQA----------ESNLSSKFQFSS     34

PDGF-D   D-ESNHLTDLYRRDETIQVKGNGYYQSPRFPNSYPRNLL          79
PDGF-C   NKEQMGVQQPQHERIIT-VSTNGSIHSPRFDHTYPRNTVL         73

PDGF-D   ITHRL-HSQENTRIQLYFQNQFGLEEAENDICRYQFVEVED       118
PDGF-C   VMRL-VAVEENVMIQLTEDEREGLEDPEDDICKYQFVEVEE       113

PDGF-D   ISEISIIRGMCGHKEYPPRTKSRTNQIKITFKSDQYFV          158
PDGF-C   PISD--GTILGRMCGSGTVPGKQISKGMQIREVSDEYFP         151

PDGF-D   AKPGFKIYYSLLEDFQPAAASETNMESVTSSISGVSYNSP        198
PDGF-C   SEDGECIHYNIVMPQFTEAV----------SP                173

PDGF-D   SVIQP-ILIADALQKKIAEFDTVEDLLKYFNPESMQEDLE        237
PDGF-C   SSVLPPSALPLDLLNNAITAESILEDIIRYLEPERMQLQLE       213

PDGF-D   HMYLDTPRYRGRSYHQ-RKSKVQLDRLN-QDAKRYSCTPR        275
PDGF-C   DLYRPDIMQLLGKAFVFGRKSRVDLNLLTEEVRLYSCTPR       253

PDGF-D   NYSVNIREELKLANVYFPRCLLVQRCGGNCGCGTVNMRS         315
PDGF-C   WFSYSIREELKRTDTIEWPGLLYKRCGGNCACLHNCNE         293

PDGF-D   CICNSGKIYKKYHEVLQFEPGHIKRRAKIMALYDIQLD          355
PDGF-C   LQCVPSKVTKKYHEVLQLRP-KTGVRG--LHKSLTDVALE        330

PDGF-D   HHERCDCICSSRPPR                                 370
PDGF-C   HHELCDCVCRGSTGG                                 345
```

▨ Signal Sequence
▨ CUB
▨ PDGF

```
MKFLVGILVA  VCLHQYLLNA  DSTKTWSEVF  ENSGCKPRPM  VFRVHDEHPE
LTSQRFNPPC  VTLMRCGGCC  NDESLECVPT  EEANVTMQLM  GASVSGGNGM
QHLSFVEHKK  CDCKPPLTTT  PPTTRPPRR   RR
```

Figure 8
Amino Acid Sequence of VEGF-E of ORF Virus
GenBank Accession No. AAO31702

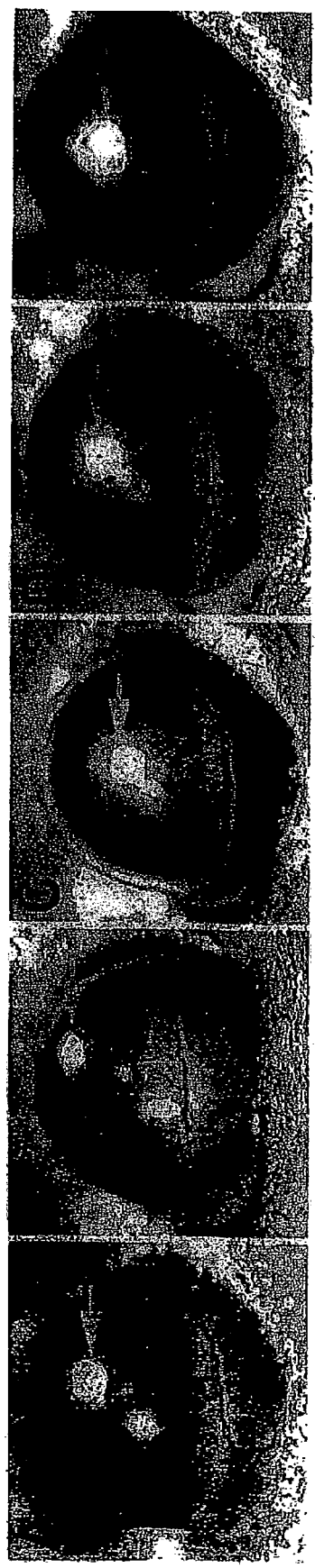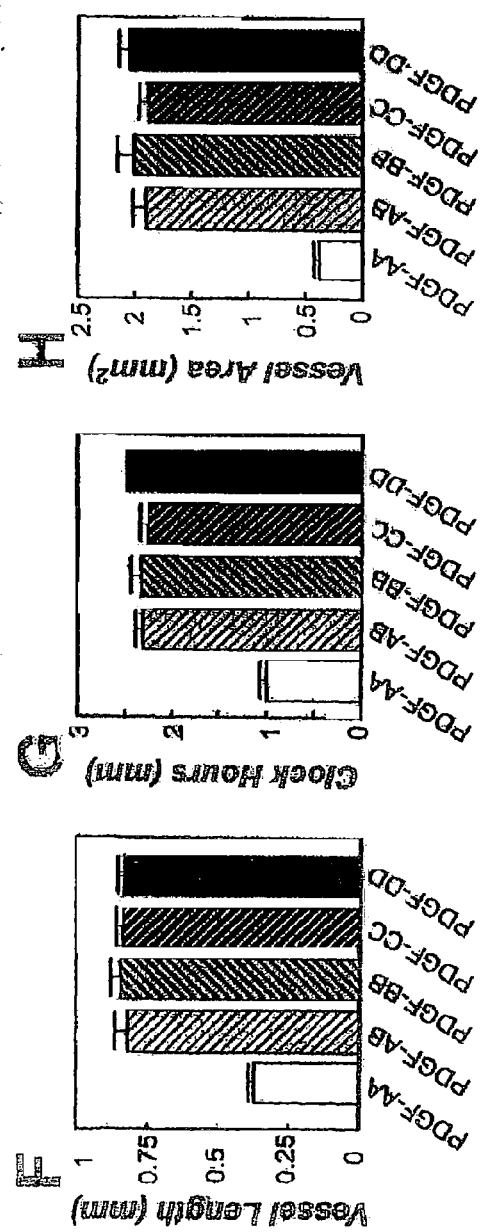
Fig. 10

METHOD FOR MODULATING, REGULATING AND/OR STABILIZING ANGIOGENESIS

CROSS-REFERENCES TO RELATED APPLICATIONS

This application claims priority of U.S. Provisional Application Ser. No. 60/550,327, filed Mar. 8, 2004, the content of which is incorporated herein by reference in its entirety.

FIELD OF THE INVENTION

This invention relates to the use of PDGF-D to modulate, regulate and/or stabilize angiogenesis, especially angiogenesis induced by angiogenic growth factors such as the various members of the VEGF family of growth factors, particularly VEGF-E.

BACKGROUND OF THE INVENTION

In the developing embryo, the primary vascular network is established by in situ differentiation of mesodermal cells in a process called vasculogenesis. It is believed that all subsequent processes involving the generation of new vessels in the embryo and neovascularization in adults, are governed by the sprouting or splitting of new capillaries from the pre-existing vasculature in a process called angiogenesis (Pepper et al., 1996, *Enzyme & Protein*, 49:38-162; Breier et al., 1995, *Dev. Dyn.*, 204:228-239; Risau, 1997, *Nature*, 386:671-674). Angiogenesis is not only involved in embryonic development and normal tissue growth, repair, and regeneration, but is also involved in the female reproductive cycle, establishment and maintenance of pregnancy, and in repair of wounds and fractures. In addition to angiogenesis which takes place in the normal individual, angiogenic events are involved in a number of pathological processes, notably tumor growth and metastasis, and other conditions in which blood vessel proliferation, especially of the microvascular system, is increased, such as diabetic retinopathy, psoriasis and arthropathies. Modulation, regulation and/or stabilization of angiogenesis is useful in preventing or alleviating various pathological processes.

On the other hand, promotion of angiogenesis is desirable in situations where vascularization is to be established or extended, for example after tissue or organ transplantation, or to stimulate establishment of collateral circulation in tissue infarction or arterial stenosis, such as in coronary heart disease and thromboangitis obliterans.

The angiogenic process is highly complex and involves the maintenance of the endothelial cells in the cell cycle, degradation of the extracellular matrix, migration and invasion of the surrounding tissue and finally, tube formation. The molecular mechanisms underlying the complex angiogenic processes are far from being understood.

Because of the crucial role of angiogenesis in so many physiological and pathological processes, factors involved in the control of angiogenesis have been intensively investigated. A number of growth factors have been shown to be involved in the regulation of angiogenesis; these include fibroblast growth factors (FGFs), platelet-derived growth factor (PDGF), transforming growth factor alpha (TGFα), and hepatocyte growth factor (HGF). See for example Folkman et al., 1992, *J. Biol. Chem.*, 267:10931-10934 for a review.

It has been suggested that a particular family of endothelial cell-specific growth factors, the vascular endothelial growth factors (VEGFs), and their corresponding receptors are primarily responsible for stimulation of endothelial cell growth and differentiation, and for certain functions of the differentiated cells. These factors are members of the PDGF family, and appear to act primarily via endothelial receptor tyrosine kinases (RTKs).

The VEGF family members share a VEGF homology domain which contains the six cysteine residues which form the cysteine knot motif. Functional characteristics of the VEGF family include varying degrees of mitogenicity for endothelial cells, induction of vascular permeability and angiogenic and lymphangiogenic properties.

Similarity between two proteins is determined by comparing the amino acid sequence and conserved amino acid substitutions of one of the proteins to the sequence of the second protein, whereas identity is determined without including the conserved amino acid substitutions.

PDGF/VEGF family members act primarily by binding to receptor tyrosine kinases. Five endothelial cell-specific receptor tyrosine kinases have been identified, namely VEGFR-1 (Flt-1), VEGFR-2 (KDR/Flk-1), VEGFR-3 (Flt4), Tie and Tek/Tie-2. All of these have the intrinsic tyrosine kinase activity which is necessary for signal transduction. The essential, specific role in vasculogenesis and angiogenesis of VEGFR-1, VEGFR-2, VEGFR-3, Tie and Tek/Tie-2 has been demonstrated by targeted mutations inactivating these receptors in mouse embryos.

The only receptor tyrosine kinases known to bind VEGFs are VEGFR-1, VEGFR-2 and VEGFR-3. VEGFR-1 and VEGFR-2 bind VEGF with high affinity, and VEGFR-1 also binds VEGF-B and PlGF. VEGF-C has been shown to be the ligand for VEGFR-3, and it also activates VEGFR-2 (Joukov et al., 1996, *The EMBO Journal*, 15:290-298). VEGF-D binds to both VEGFR-2 and VEGFR-3. VEGF-E binds with high affinity to VEGFR-2 and neuropilin-1, but neither to VEGFR-1 nor to VEGFR-3, inducing vascular permeability and potent angiogenic activity both in vitro and in vivo (Ogawa et al., J. Biol. Chem. 1998. 273: 31273-31282; Meyer et al., EMBO J. 1999. 18: 363-374; Wise et al., Proc. Natl. Acad. Sci. USA 1999. 96: 3071-3076.). A ligand for Tek/Tie-2 has been described in International Patent Application No. PCT/US95/12935 (WO 96/11269) by Regeneron Pharmaceuticals, Inc. The ligand for Tie has not yet been identified.

The isolation and cloning of a novel 130-135 kDa VEGF isoform specific receptor has been reported in Soker et al., 1998, *Cell*, 92:735-745. This VEGF receptor was found to specifically bind the VEGF$_{165}$ isoform via the exon 7 encoded sequence, which shows weak affinity for heparin (Soker et al., 1998, *Cell*, 92:735-745). Surprisingly, the receptor was shown to be identical to human neuropilin-1 (NP-1), a receptor involved in early stage neuromorphogenesis. PlGF-2 also appears to interact with NP-1 (Migdal et al., 1998, *J. Biol. Chem.*, 273:22272-22278).

VEGFR-1, VEGFR-2 and VEGFR-3 are expressed differently by endothelial cells. Both VEGFR-1 and VEGFR-2 are expressed in blood vessel endothelia (Oelrichs et al., 1992, *Oncogene*, 8:11-18; Kaipainen et al., 1993, *J. Exp. Med.*, 178:2077-2088; Dumont et al., 1995, *Dev. Dyn.*, 203:80-92; Fong et al., 1996, *Dev. Dyn.*, 207:1-10) and VEGFR-3 is mostly expressed in the lymphatic endothelium of adult tissues (Kaipainen et al., 1995, *Proc. Natl. Acad. Sci. USA*, 9:3566-3570). VEGFR-3 is also expressed in the blood vasculature surrounding tumors.

Disruption of the VEGFR genes results in aberrant development of the vasculature leading to embryonic lethality around midgestation. Analysis of embryos carrying a completely inactivated VEGFR-1 gene suggests that this receptor is required for functional organization of the endothelium (Fong et al., 1995, *Nature*, 376:66-70). However, deletion of the intracellular tyrosine kinase domain of VEGFR-1 generates viable mice with a normal vasculature (Hiratsuka et al., 1998, *Proc. Natl. Acad. Sci. USA*, 95:9349-9354). The reasons underlying these differences remain to be explained but suggest that receptor signaling via the tyrosine kinase is not required for the proper function of VEGFR-1. Analysis of homozygous mice with inactivated alleles of VEGFR-2 suggests that this receptor is required for endothelial cell proliferation, hematopoesis and vasculogenesis (Shalaby et al., 1995, *Nature*, 376:62-66; Shalaby et al., 1997, *Cell*, 89:981-990). Inactivation of VEGFR-3 results in cardiovascular failure due to abnormal organization of the large vessels (Dumont et al., 1998, *Science*, 282:946-949).

Although VEGFR-1 is mainly expressed in endothelial cells during development, it can also be found in hematopoetic precursor cells during early stages of embryogenesis (Fong et al., 1995, *Nature*, 376:66-70). It is also is expressed by most, if not all, vessels in embryos (Breier et al., 1995, *Dev. Dyn.*, 204:228-239; Fong et al., 1996, *Dev. Dyn.*, 207:1-10). In adults, monocytes and macrophages also express this receptor (Barleon et al., 1996, *Blood*, 87:3336-3343).

The receptor VEGFR-3 is widely expressed on endothelial cells during early embryonic development, but as embryogenesis proceeds, it becomes restricted to venous endothelium and then to the lymphatic endothelium (Kaipainen et al., 1994, *Cancer Res.*, 54:6571-6577; Kaipainen et al., 1995, *Proc. Natl. Acad. Sci. USA*, 92:3566-3570). VEGFR-3 continues to be expressed on lymphatic endothelial cells in adults. This receptor is essential for vascular development during embryogenesis. Targeted inactivation of both copies of the VEGFR-3 gene in mice resulted in defective blood vessel formation characterized by abnormally organized large vessels with defective lumens, leading to fluid accumulation in the pericardial cavity and cardiovascular failure at post-coital day 9.5. On the basis of these findings it has been proposed that VEGFR-3 is required for the maturation of primary vascular networks into larger blood vessels. However, the role of VEGFR-3 in the development of the lymphatic vasculature could not be studied in these mice because the embryos died before the lymphatic system emerged. Nevertheless it is assumed that VEGFR-3 plays a role in development of the lymphatic vasculature and lymphangiogenesis given its specific expression in lymphatic endothelial cells during embryogenesis and adult life. This is supported by the finding that ectopic expression of VEGF-C, a ligand for VEGFR-3, in the skin of transgenic mice, resulted in lymphatic endothelial cell proliferation and vessel enlargement in the dermis. Furthermore this suggests that VEGF-C may have a primary function in lymphatic endothelium, and a secondary function in angiogenesis and permeability regulation which is shared with VEGF (Joukov et al., 1996, *EMBO J.*, 15:290-298).

PDGF plays an important role in the growth and/or motility of connective tissue cells, fibroblasts, myofibroblasts and glial cells (Heldin et al., "Structure of platelet-derived growth factor: Implications for functional properties", 1993, *Growth Factor*, 8:245-252). In adults, PDGF stimulates wound healing (Robson et al., 1992, *Lancet*, 339:23-25). Structurally, PDGF isoforms are disulfide-bonded dimers of homologous A- and B-polypeptide chains, arranged as homodimers (PDGF-AA and PDGF-BB) or a heterodimer (PDGF-AB).

PDGF isoforms exert their effects on target cells by binding to two structurally related receptor tyrosine kinases (RTKs). The alpha-receptor binds both the A- and B-chains of PDGF, whereas the beta-receptor binds only the B-chain. These two receptors are expressed by many cell lines grown in vitro, and are mainly expressed by mesenchymal cells in vivo. The PDGFs regulate cell proliferation, cell survival and chemotaxis of many cell types in vitro (reviewed in Heldin et al., 1998, *Biochim. Biophys. Acta*, 1378:F79-113). In vivo, they exert their effects in a paracrine mode since they often are expressed in epithelial (PDGF-A) or endothelial cells (PDGF-B) in close apposition to the PDGFR expressing mesenchyme. In tumor cells and in cell lines grown in vitro, coexpression of the PDGFs and the receptors generate autocrine loops which are important for cellular transformation (Betsholtz et al., 1984, *Cell*, 39:447-57; Keating et al., 1990, *J. R. Coll Surg Edinb.*, 35:172-4). Overexpression of the PDGFs have been observed in several pathological conditions, including malignancies, arteriosclerosis, and fibroproliferative diseases (reviewed in Heldin et al., 1996, *The Molecular and Cellular Biology of Wound Repair*, New York: Plenum Press, 249-273).

The importance of the PDGFs as regulators of cell proliferation and survival are well illustrated by recent gene targeting studies in mice that have shown distinct physiological roles for the PDGFs and their receptors despite the overlapping ligand specificities of the PDGFRs. Homozygous null mutations for either of the two PDGF ligands or the receptors are lethal. Approximately 50% of the homozygous PDGF-A deficient mice have an early lethal phenotype, while the surviving animals have a complex postnatal phenotype with lung emphysema due to improper alveolar septum formation because of a lack of alveolar myofibroblasts (Boström et al., 1996, *Cell*, 85:863-873). The PDGF-A deficient mice also have a dermal phenotype characterized by thin dermis, misshapen hair follicles and thin hair (Karlsson et al., 1999, *Development*, 126:2611-2). PDGF-A is also required for normal development of oligodendrocytes and subsequent myelination of the central nervous system (Fruttiger et al., 1999, *Development*, 126:457-67). The phenotype of PDGFR-alpha deficient mice is more severe with early embryonic death at E10, incomplete cephalic closure, impaired neural crest development, cardiovascular defects, skeletal defects, and edemas (Soriano et al., 1997, *Development*, 124:2691-70). The PDGF-B and PDGFR-beta deficient mice develop similar phenotypes that are characterized by renal, hematological and cardiovascular abnormalities (Leveen et al., 1994, *Genes Dev.*, 8:1875-1887; Soriano et al., 1994, *Genes Dev.*, 8:1888-96; Lindahl et al., 1997, *Science*, 277:242-5; Lindahl, 1998, *Development*, 125:3313-2), where the renal and cardiovascular defects, at least in part, are due to the lack of proper recruitment of mural cells (vascular smooth muscle cells, pericytes or me sangial cells) to blood vessels (Levéen et al., 1994, *Genes Dev.*, 8:1875-1887; Lindahl et al., 1997, *Science*, 277:242-5; Lindahl et al., 1998, *Development*, 125:3313-2).

A member of the PDGF family of growth factors is PDGF-D, which is described in International patent application no. WO 00/27879 and published US application no. 2002/0164710 A1, the entire contents of which are incorporated herein by reference. PDGF-D has the ability to stimulate, or enhance, or both, one or more of proliferation, differentiation, growth, and motility of cells expressing a PDGF-D receptor. Cells affected by PDGF-D include, but are not limited to, endothelial cells, connective tissue cells, myofibroblasts and glial cells. PDGF-D and compositions containing it are useful for various therapeutic applications involving the modulation, regulation and/or stabilization of angiogenesis, and particularly for the treatment of edemas which result from leaky vessels.

PDGF-D is structurally homologous to PDGF-A, PDGF-B, VEGF, VEGF-B, VEGF-C and VEGF-D. The polynucleotide sequence of at least nucleotides 935 to 1285 set out in FIG. 2 (SEQ ID NO:1) encodes a portion of the PDGF/VEGF homology domain, which is the bioactive fragment of PDGF-D. The bioactive fragment is also included in the 200 amino acids set out in FIG. 3 (SEQ ID NO:3) (excluding the first 24 amino acid residues, which are due to a cloning artifact) or the 322 amino acid sequence set out in FIG. 4 (SEQ ID NO:4).

PDGF-D has the ability to stimulate one or more of proliferation, differentiation, motility, survival or vascular permeability of cells expressing a PDGF-D receptor including, but not limited to, vascular endothelial cells, lymphatic endothelial cells, connective tissue cells (such as fibroblasts), myofibroblasts and glial cells. PDGF-D also has the ability to stimulate wound healing. A preferred fragment is a truncated form of PDGF-D comprising a portion of the PDGF/VEGF homology domain (PVHD) of PDGF-D. The portion of the PVHD is from residues 254-370 of FIG. 1 (SEQ ID NO:2) where the putative proteolytic processing site RKSK starts at amino acid residue 254 (SEQ ID NO:2). However, the PVHD extends toward the N terminus up to residue 234 of FIG. 1 (SEQ ID NO:2). Herein the PVHD is defined as truncated PDGF-D. The truncated PDGF-D is the putative activated form of PDGF-D.

As indicated above, there are numerous clinical situations where angiogenesis is desired to be promoted, and methods have been proposed using one of the numerous members of the VEGF/PDGF family of growth factors known to have angiogenesis stimulation effects. For example, VEGF has been shown to be intimately involved in the entire sequence of events leading to growth of new blood vessels. Gross et al., Proc. Nat'l. Acad. Sci., 80(9): 2623-27 (1983), Folkman et al., Proc. Nat'l. Acad. Sci., 76(10): 5217-21 (1979). Five human VEGF isoforms of 121, 145, 165, 189 and 206 amino acids have been isolated. Gross, et al., Proc. Nat'l. Acad. Sci., 80(9): 2623-27 (1983), Leung, et al., Science, 246: 1306-09 (1989), Poltorak et al., J. Biol. Chem., 272(11): 7151-78 (1997). Among the isoforms, VEGF 165 seems to be the most effective and most commonly used. The effect of VEGF 165 in augmenting perfusion and in stimulating formation of collateral vessels has been shown in animal models Hopkins et al., J. Vascular Surgery, 27(5): 886-94 (1998), Asahara et al., Circulation, 91(11): 2793-801 (1995), Hariawala et al., J. Surg. Res., 63(1): 77-82 (1996), Bauters et al., Circulation, 91(11): 2802-9 (1995), Bauters et al., Am. J. Physiol., 267(4 Pt 2): H1263-71 (1994), Takeshita et al., J. Clin. Invest., 93(2): 662-70 (1994), Takeshita, et al., Circulation, 90(5 Pt 2): II228-34 (1994), Takeshita, et al., Am. J. Path., 147(6): 1649-60 (1995), Banai, et al., Circulation, 89(5): 2183-9 (1994). In clinical trials, successful induction of collateral blood vessels in ischemic heart disease and critical limb ischemia by VEGF have also been reported. Baumgartner et al., Circulation, 97(12): 1114-23 (1998), Losordo, et al., Am. Heart J., 138(2 Pt 2): 132-41 (1999).

Angiogenesis, however, is a complex process that includes activation, migration and proliferation of endothelial cells and formation of new blood vessels. D'Amore, et al., Ann. Rev. Physiol., 49(9-10): 453-64 (1987). The process likely requires a network of members of the VEGF/PDGF family of growth factors, and use of a single factor alone in promoting angiogenesis may have undesired or unsatisfactory results. For example, it is known that the vascular endothelial growth factor-A ("VEGF") causes both abnormal blood vessel growth (angiogenesis) and blood vessel leakage in the eye. Specifically, preclinical studies have shown that a) in multiple animal species, including humans, VEGF levels are elevated around growing and leaky blood vessels, b) blocking VEGF results in the prevention and regression of these abnormal vessels in primates and other species and c) VEGF alone is sufficient to trigger the abnormal blood vessel growth and blood vessel leakage that characterizes wet age-related macular degeneration (AMD). See A. P. Adamis et al., Inhibition of vascular endothelial growth factor prevents retinal ischemia-associated iris neovascularization in a nonhuman primate, 114(1) Arch. Ophthalmol. 66-71 (1996); A. Kvanta et al., Subfoveal fibrovascular membranes in age-related macular degeneration express vascular endothelial growth factor, 37 Invest. Ophthalmol. Vis. Sci. 1929-34 (1996); G. Lutty et al., Localization of VEGF in human retina and choroids, 114 Arch. Ophthalmol. 971-77 (1996); M. J. Tolentino et al., Intravitreous injections of vascular endothelial growth factor produce retinal ischemia and microangiopathy in an adult primate, 103(11) Ophthalmology 1820-28 (1996); M. J. Tolentino, Vascular endothelial growth factor is sufficient to produce iris neovascularization and neovascular glaucoma in a nonhuman primate, 114(8) Arch. Ophthalmol. 964-70 (1996). To minimize the undesired effect of VEGF, VEGF antagonists have been proposed, but these antagonists are obviously not suitable for situations where stimulation of angiogenesis is desired.

Thus, there is a significant need to be able to modulate the angiogenesis promoting activities of one member of the PDGF/VEGF family of growth factors, preferably with another member of the family.

SUMMARY OF THE INVENTION

It has now been found that PDGF-D can act to modulate, regulate and/or stabilize angiogenesis.

In particular, it has been found that PDGF-D can act to stabilize the vessels induced by angiogenic activity of other angiogenic growth factors, such as members of the VEGF family of growth factors, particularly VEGF-E.

According to the present invention, any polypeptide sequence having a VEGF-E activity is suitable. For example, VEGF-E derivatives, variants and analogs are suitable and include polypeptides that are at least 70% or at least 80% identical to SEQ ID NO:15 (FIG. 8). In this regard, polypeptides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

It has additionally been found that PDGF-D can act to reduce the leakage of leaky vessels, by for example inducing or stimulating the proliferation and migration of smooth muscle cells (SMC).

Another aspect of the invention provides for the use of vectors comprising PDGF-D DNA and host cells transformed or transfected with nucleic acid molecules or vectors of the invention. These may be eukaryotic or prokaryotic in origin. These cells are particularly suitable for expression of the polypeptide of the invention, and include insect cells such as Sf9 cells, obtainable from the American Type Culture Collection (ATCC SRL-171), transformed with a baculovirus vector, and the human embryo kidney cell line 293-EBNA transfected by a suitable expression plasmid. Preferred vectors of the invention are expression vectors in which a nucleic acid according to the invention is operatively connected to one or more appropriate promoters and/or other control sequences, such that appropriate host cells transformed or transfected with the vectors are capable of expressing the polypeptide of the invention. Other preferred vectors are those suitable for transfection of mammalian cells, or for gene therapy, such as adenoviral-, adeno-associated virus, vaccinia- or retroviral-based vectors or liposomes. A variety of such vectors is known in the art. These vectors may be used to generate PDGF-D in situ to modulate, regulate and/or stabilize angiogenic activity.

Clinical applications of the invention include stabilization of angiogenesis in tissue or organ transplantation to promote graft growth and vascularization, or in wound healing, or in connective tissue development, or in the establishment of collateral circulation in tissue infarction or arterial stenosis, such as coronary artery disease.

The angiogenesis-modulating and/or stabilizing effects of PDGF-D may also be relevant to a variety of lung conditions. PDGF-D could be used in the treatment of lung disorders to improve blood circulation in the lung and/or gaseous exchange between the lungs and the blood stream. Similarly, PDGF-D could be used to improve blood circulation to the heart and $O_2$ gas permeability in cases of cardiac insufficiency. In a like manner, PDGF-D could be used to improve blood flow and gaseous exchange in chronic obstructive airway diseases.

Thus the invention provides a method for stabilizing, regulating or modulating angiogenesis, lymphangiogenesis, neovascularization, connective tissue development and/or wound healing in a mammal in need of such treatment, comprising the step of administering an effective dose of PDGF-D, or a fragment or an analog thereof which has the biological activity of PDGF-D to the mammal. The PDGF-D polypeptides may be administered either in the form of its bioactive fragment (e.g. residues 254-370 of SEQ ID NO:2), or in the form of a full-length sequence which may be activated, e.g. with a suitable protease, in situ. Alternatively, a nucleic acid molecule coding for a bioactive PDGF-D polypeptide may be administered, or a nucleic acid molecule coding for a full-length PDGF-D polypeptide together with a nucleic acid molecule coding for a suitable protease are administered together, preferably under the control of regulatory elements suitable for regulation of their respective expression. Optionally the PDGF-D, or fragment or analog thereof may be administered together with, or in conjunction with, one or more of VEGF, VEGF-B, VEGF-C, VEGF-D, PlGF, PDGF-A, PDGF-B, PDGF-C, FGF and/or heparin.

PDGF-D polypeptides may be directly delivered to the site of interest where angiogenesis etc are desired. Numerous direct polypeptide delivery methods are known and may be used. See e.g. Talmadge, 1993, The pharmaceutics and delivery of therapeutic polypeptides and proteins, *Adv. Drug Del. Rev.* 10:247-299. The polypeptides may be administered orally. Although polypeptides are generally known to have poor availability through oral administration, various methods known in the art have been developed to overcome this limitation. For example, biodegradable polymeric matrices have been used for delivering proteins over a desired period of time. For example, the use of biodegradable poly(d, l-lactic-co-glycolic acid) (PLGA) microspheres for the delivery of peptides and proteins has been widely reported (Mehta et al., 1996, Peptide containing microspheres from low molecular weight and hydrophilic poly(d,l-lactide-co-glycolide), *J. Control Release* 41:249-257; Chiba et al., 1997, Controlled protein delivery from biodegradable tyrosine-containing poly (anhydride-co-imide) microspheres. *Biomaterials* 18:893-901; Ravivarapu et al., 2000, Polymer and microsphere blending to alter the release of a peptide from PLGA microspheres, *Eur. J. Pharm. Biopharm.* 50:263-270).

Preferably, direct application of the polypeptides, especially direct injection, or topical application, may be used. Because wound-healing and other conditions requiring enhanced angiogenesis typically require local application of PDGF-D polypeptides and other growth factors for only a limited time, direct injection, even frequent direct injection of the polypeptides to the desired site(s) is acceptable and is not likely to be very tedious or expensive and pose problems such as poor patient acceptance. Methods of direct application of polypeptides are well-known to those ordinarily skilled in the art, and recent successes, strategies, and potentials of topical application of PDGF-BB in improving healing were reviewed by Cupp et al., 2002, Gene therapy, electroporation, and the future of wound-healing therapies, *Facial Plast. Surg.* 18:53-57.

In another preferred embodiment, the therapeutic polypeptides of the present invention may be delivered in the form of nucleic acid molecules encoding the polypeptides. Many established and well-known methods for gene delivery or gene therapy may be used for administering genes or other nucleic acid molecules encoding PDGF-D to the patient. See e.g. Rubany, 2001, The future of human gene therapy, *Mol. Aspects. Med.* 22:113-42. A single dose of naked DNA of VEGF and PDGF was used to treat rats with cysteanmine-induced duodenal ulcers, and was shown to significantly accelerate chronic duodenal ulcer healing, and increase VEGF and PDGF levels in duodenal mucosa (Szabo et al., 2001, Gene Expression and gene therapy in experimental duodena ulceration, *J. Physiol. Paris* 95:325-335).

The polynucleotides encoding PDGF-D preferably are linked operatively under the control of suitable promoter so that they are expressed when taken up by the host cells. PDGF-D is a diffusible protein, and as such it will exert its effects on cells directly expressing the polypeptides, as well as on surrounding cells. Accordingly, suitable promoters may be constitutive promoters such as promoter and enhancer elements from cytomegalovirus (CMV), Rous sarcoma virus (RSV), and SV40, and the rat beta-actin promoter. Preferably, inducible or tissue specific promoters are used to increase expression level, improve specificity and reduce side effects. In this regard, suitable promoters include the keratin 5 (K5) promoter (Pierce et al., 1998, *Oncogene* 16: 1267-1276; Pierce et al., 1998, *Proc. Natl. Acad. Sci. USA* 95:8858-8863), the Cyr61 promoter (inducible in granulation tissue during wound healing) (Latinkic et al., 2001, Promoter function of the angiogenic inducer Cyr61 gene in transgenic mice: tissue specificity, inducibility during wound healing, and role of the serum response element, *Endocrinol.* 142:2549-2557), and the FAP promoter (Neidermeyer et al., 2001, Expression of the fibroblast activation protein during mouse embryo development, *Int. J. Dev. Biol.* 45:445-447).

Suitable polynucleotides may also be delivered as nonviral vectors, using methods well-known to those ordinarily skilled in the art. See e.g. Brown et al., 2001, Gene delivery with synthetic (non-viral) carriers, *Int. J. Pharm.* 229:1-21; and Pouton et al., 1998, Key issues in non-viral gene delivery, *Adv. Drug Deliv. Rev.* 34:3-19.). Lipofection, liposome mediated gene transfer are preferred (Romano et al., 1999, Gene transfer technology in therapy: current applications and future goals. *Stem Cells* 17:191-202; Mountain, 2000, Gene therapy: the first decade. *Trends. Biotechnol.* 18:119-28; Mhashilkar et al., 2001, Gene therapy: Therapeutic approaches and implications. *Biotechnol. Adv.* 19:279-97; and Lasic, 1998, Novel applications of liposomes, *Trends Biotechnol.* 16:307-21).

One of the simplest ideas for non-viral gene delivery is the use of purified DNA in the form of plasmids. A naked polynucleotide operatively coding for the polypeptide may be delivered, along with a pharmaceutically acceptable carrier, directly to the desired site, where the polynucleotide is taken up by the cells at the site and expressed or otherwise exerts its therapeutic effects. This is particularly preferred if transient expression of the gene is desired. The transfer of naked DNA by physical means is well known, by such means as gene guns and electroporation. See e.g. Spack et al., 2001, Developing non-viral DNA delivery systems for cancer and infectious disease, *DDT* 6:186-97. See also Cupp et al., 2002, supra.

In general, RNA molecules will have more transient effects than DNA molecules. The effects of the naked RNA molecules so delivered last typically for less than about 20 days, usually less than 10 days, and often less than 3 to 5 days. Delivery may be by injection, spray, biolistic methods, and so on, depending on the site.

In another embodiment, suitable polynucleotides may also be delivered within viral vectors, which are known to have higher transfection efficiency compared to nonviral vectors. See e.g. Robbins et al., 1998, Viral vectors for gene therapy, *Pharmacol. Ther.* 80:35-47; and Kay et al., 2001, Viral vectors for gene therapy: the art of turning infectious agents into vehicles of therapeutics, *Nat. Med.* 7:33-40. Suitable viral vectors include those derived from retroviruses (including lentivirues) (see e.g. Breithart et al., 1999, *Ann. Plast. Surg.* 43:632-9), especially the Moloney murine leukemia virus and pseudotyped retroviruses (Chen et al., 2001, Safety testing for replication-competent retrovirus associated with gibbon ape leukemia virus-pseudotyped retroviral vectors. *Hum. Gene. Ther.* 12:61-70); adenoviruses, especially the third generation "gutless" adenoviral vector (Kochanek et al., 2001, High-capacity "gutless" adenoviral vectors. *Curr. Opin. Mol. Ther.* 3:454-63.); chimeric viruses that combine the advantages of both retroviruses and adenoviruses (Reynolds et al., 1999, Chimeric viral vectors-the best of both worlds? *Mol. Med. Today* 5:25-31, 1999); adeno-associated virus (Ponnazhagan et al., 2001, Adeno-associated virus for gene therapy. *Cancer Res.*, 61:6313-21; and Monahan et al., 2000, Adeno-associated virus vectors for gene therapy: more pros than cons? *Mol. Med. Today*, 6:433-40.); vaccinia viruses (Peplinski, et al., 1998, Vaccinia virus for human gene therapy. *Surg. Oncol. Clin. N. Am.*, 7:575-588); and herpes simplex virus (Latchman. 2001, Gene delivery and gene therapy with herpes simplex virus-based vectors. *Gene* 264:1-9).

Adenoviral vectors are preferred. Chen et al. (2002) showed that recombinant adenoviruses encoding the PDGF-A gene express and secrete PDGF-A in vitro, and induce sustained down regulation of PDGFαR encoded by the growth arrest specific (gas) gene (Am. J. Physiol. Cell Physiol. 282:C538-44). Szabo et al., supra, used a single dose of adenoviral vectors expressing VEGF and PDGF to treat rats with cysteanmine-induced duodenal ulcers, and showed significant acceleration of chronic duodenal ulcer healing, and increased VEGF and PDGF levels in duodenal mucosa. Giannobile et al., 2001, *J. Periodontol.* 72:815-23 showed that adenoviral vectors expressing PDGF-A stimulated cementoblast DNA synthesis and subsequent proliferation. Zhu et al., 2001, *J. Dent. Res.* 80:892-7 demonstrated that adenoviruses encoding PDGF-A enhanced mitogenic and proliferative responses in osteoblasts, periodontal ligament fibroblasts and gingival fibroblasts. See also Liechty et al., 1999, Adenoviral mediated overexpression of PDGF-B corrects ischemic impaired wound healing, *J. Invest. Dermatol.* 113:375-83.

The effects of vectors coding for PDGF-D polypeptides may also be improved with matrix immobilization to enhance tissue repair activity. Biocompatible matrices capable of immobilizing adenoviral vectors have been successfully used in treating ischemic excisional wounds. Specifically, collagen-formulated vectors encoding PDGF-B, when delivered as subcutaneously implanted sponges, have been shown to enhance granulation tissue deposition, enhance epithelial area, and improve wound closure more effectively than aqueous formulations of the same vectors. With longer time, complete healing without excessive scar formation was achieved. In comparison, aqueous formulations allowed vector seepage and led to PDGF-induced hyperplasia in surrounding tissues but not in wound beds. In addition, repeated applications of PDGF-BB proteins were required for neotissue induction approaching equivalence to a single application of collagen-immobilized vectors. (Doukas et al., 2002, *Hum. Gene Ther.* 12:783-98). In the same study, Doukas et al. also showed that vectors encoding fibroblast growth factor 2 or vascular endothelial growth factor promoted primarily angiogenic responses. Similar improvements were observed in dermal ulcer wounds in the ears of young adult New Zealand white rabbits with collagen embedded PDGF-B or PDGF-A DNA plasmids (Tyrone et al., 2000, *J. Surg. Res.* 93:230-6); in soft tissue repair by enhancing de novo tissue formation (Chandler et al., 2000, *Mol. Ther.* 2:153-60).

Other materials may also be used as sustained release matrices for delivering vectors encoding PDGF genes. For example, matrices of poly(lactide-co-glycolide) (PLG) were loaded with plasmids and shown to release the plasmids over a period ranging from days to months in vitro, and led to the transfection of large numbers of cells. In vivo delivery enhanced matrix deposition and blood vessel formation in the developing tissue (Shea et al., 1999, *Nat. Biotechnol.* 17:551-4).

Another method of gene delivery uses fusigenic virosomes. This approach combines some of the advantages of viral delivery vectors with the safety and 'simplicity' of the liposome to produce fusigenic virosomes (Dzau et al., 1996, Fusigenic viral liposome for gene therapy in cardiovascular diseases. *Proc Natl. Acad. Sci. USA* 93:11421-25). Virosomes have been engineered by complexing the membrane fusion proteins of hemagglutinating virus of Japan (HVJ, which is also known as Sendai virus) with either liposomes that already encapsulate plasmid DNA or oligodeoxynucleotides (ODN) for antisense applications. The inherent ability of the viral proteins in virosomes to cause fusion with cell membranes means that these hybrid vectors can be very efficient at introducing their nucleic acid to the target cell, resulting in good gene expression. Each viral vector has a limit on the size of transgene that can be incorporated into its genome; no such limit exists for virosome or liposome technology. Genes of up to 100 kilobase pairs have been delivered by fusigenic virosomes to cells both ex vivo and in vivo.

A further embodiment of the invention utilizes DNA-ligand conjugates for delivery of genes encoding the PDGF-polypeptides. DNA-ligand conjugates have two main components: a DNA-binding domain and a ligand for cell-surface receptors. The transgene can therefore be guided specifically to the target cell, where it is internalized via receptor-mediated endocytosis. Once the DNA-ligand complex is in the endocytic pathway, the conjugate is likely to be destroyed when the endosome fuses with a lysosome. To avoid this, an adenovirus-derived domain may be incorporated into the cell-surface receptor part of the ligand (Curiel et al, 1992, High-efficiency gene transfer mediated by adenovirus coupled to DNA-polylysine complexes, *Hum. Gene Ther.* 3:147-154). The conjugates then have the same specificity as adenoviruses, binding to a wide host-cell range; they also possess an adenovirus characteristic that allows the conjugate to leave the endosome and enter the cytoplasm (by a process known as endosomolysis) before the endosome is destroyed by a lysosome.

According to another embodiment of the invention, suitable host cells may be transformed with polynucleotides, preferably vectors, more preferably viral vectors, encoding the PDGF-D polypeptides of the invention, and the host cells expressing the PDGF-D polypeptides may be introduced to a host animal in need of wound healing or other treatment. Many methods of in vitro cell transformation are known and well established in the art, including CaPO$_4$ transfection, which is a chemical method that has been successfully used by molecular biologists for many years to introduce transgenes into cells in vitro with a relatively good efficiency (10%). Mathisen et at. showed that autoreactive memory Th2 T cells can be genetically modified so that upon engagement of self antigen they produce regenerative growth factors such as PDGF-A capable of mediating tissue repair during autoimmune disease (Mathisen et al., 1999, *J. Autoimmun.* 13:31-8.

Where PDGF-D is to be used for therapeutic purposes, the dose(s) and route of administration will depend upon the nature of the patient and condition to be treated, and will be at the discretion of the attending physician or veterinarian. Suitable routes include oral, subcutaneous, intramuscular, intraperitoneal or intravenous injection, parenteral, topical application, implants etc. Topical application of PDGF-D may be used in a manner analogous to VEGF. When used for stabilizing angiogenesis, an effective amount of the truncated active form of PDGF-D is administered to an organism in need thereof in a dose between about 0.1 and 1000 μg/kg body weight.

The PDGF-D may be employed in combination with a suitable pharmaceutical carrier. The resulting compositions comprise a therapeutically effective amount of PDGF-D and a pharmaceutically acceptable non-toxic salt thereof, and a pharmaceutically acceptable solid or liquid carrier or adjuvant. Examples of such a carrier or adjuvant include, but are not limited to, saline, buffered saline, Ringer's solution, mineral oil, talc, corn starch, gelatin, lactose, sucrose, microcrystalline cellulose, kaolin, mannitol, dicalcium phosphate, sodium chloride, alginic acid, dextrose, water, glycerol, ethanol, thickeners, stabilizers, suspending agents and combinations thereof. Such compositions may be in the form of solutions, suspensions, tablets, capsules, creams, salves, elixirs, syrups, wafers, ointments or other conventional forms. The formulation should be constituted to suit the mode of administration. Compositions which comprise PDGF-D may optionally further comprise one or more of PDGF-A, PDGF-B, PDGF-C, VEGF, VEGF-B, VEGF-C, VEGF-D, VEGF-E, PlGF and/or heparin. Compositions comprising PDGF-D will contain from about 0.1% to 90% by weight of the active compound(s), and most generally from about 10% to 30%.

For intramuscular preparations, a sterile formulation, preferably a suitable soluble salt form of the truncated active form of PDGF-D, such as hydrochloride salt, can be dissolved and administered in a pharmaceutical diluent such as pyrogen-free water (distilled), physiological saline or 5% glucose solution. A suitable insoluble form of the compound may be prepared and administered as a suspension in an aqueous base or a pharmaceutically acceptable oil base, e.g. an ester of a long chain fatty acid such as ethyl oleate.

In another aspect, the invention relates to use of a protein dimer comprising the PDGF-D polypeptide, particularly a disulfide-linked dimer. The protein dimers of the invention include both homodimers of PDGF-D polypeptide and heterodimers of PDGF-D and VEGF, VEGF-B, VEGF-C, VEGF-D, VEGF-E, PlGF, PDGF-A, PDGF-B or PDGF-C.

Another aspect of the invention relates to the discovery that the full length PDGF-D protein is likely to be a latent growth factor that needs to be activated by proteolytic processing to release an active PDGF/VEGF homology domain. A putative proteolytic site is found in residues 254-257 in the full length protein, residues -RKSK- (SEQ ID NO:5). This is a dibasic motif. The -RKSK- (SEQ ID NO:5) putative proteolytic site is also found in PDGF-A, PDGF-B, VEGF-C and VEGF-D. In these four proteins, the putative proteolytic site is also found just before the minimal domain for the PDGF/VEGF homology domain. Together these facts indicate that this is the proteolytic site.

Preferred proteases include, but are not limited, to plasmin, Factor X and enterokinase. The N-terminal CUB domain may function as an inhibitory domain which might be used to keep PDGF-D in a latent form in some extracellular compartment and which is removed by limited proteolysis when PDGF-D is needed.

According to this aspect of the invention, a method is provided for producing an activated truncated form of PDGF-D or for regulating receptor-binding specificity of PDGF-D. These methods comprise the steps of expressing an expression vector comprising a polynucleotide encoding a polypeptide having the biological activity of PDGF-D and supplying a proteolytic amount of at least one enzyme for processing the expressed polypeptide to generate the activated truncated form of PDGF-D.

This aspect also includes a method for selectively activating a polypeptide having a growth factor activity. This method comprises the step expressing an expression vector comprising a polynucleotide encoding a polypeptide having a growth factor activity, a CUB domain and a proteolytic site between the polypeptide and the CUB domain, and supplying a proteolytic amount of at least one enzyme for processing the expressed polypeptide to generate the activated polypeptide having a growth factor activity.

Also this aspect includes use of an isolated dimer comprising an activated monomer of PDGF-D and an activated monomer of VEGF, VEGF-B, VEGF-C, VEGF-D, VEGF-E, PDGF-D, PDGF-A, PDGF-B, PDGF-C or PlGF linked to a CUB domain, or alternatively, an activated monomer of VEGF, VEGF-B, VEGF-C, VEGF-D, PDGF-D, PDGF-A, PDGF-B or PlGF and an activated monomer of PDGF-D linked to a CUB domain. The isolated dimer may or may not include a proteolytic site between the activated monomer and the CUB domain.

It will be clearly understood that the PDGF-D polypeptides used in the invention may be prepared by synthetic means or by recombinant means, or may be purified from natural sources.

It will be clearly understood that for the purposes of this specification the word "comprising" means "including but not limited to." The corresponding meaning applies to the word "comprises."

BRIEF DESCRIPTION OF THE DRAWINGS

FIG. 1 (SEQ ID NO:2) shows the complete 370 amino acid sequence of full-length human PDGF-D, FIG. 2 (SEQ ID NO:1) shows the complete (1116 bp) nucleotide sequence of the cDNA which encodes hPDGF-D (SEQ ID NO:2);

FIG. 3 shows the amino acid sequence of an active 200 amino acid hPDGF-D fragment (SEQ ID NO:3).

FIG. 4 shows the amino acid sequence of a 322 amino acid active hPDGF-D fragment (SEQ ID NO:4);

FIG. 5 shows an amino acid sequence alignment of the hPDGF-D with hPDGF-C (SEQ ID NOs:2 and 6, respectively);

FIG. 8 shows the amino acid sequences of a known VEGF-E sequence from the ORF Virus (SEQ ID NO: 15), GenBank Accession No. AA031702 or AF106020.

FIG. 10 shows the in vivo angiogenic activity of human PDGF-DD and other PDGF isoforms in the mouse cornea pocket assay. The arrows in the figures point to where PDGF protein-containing beads were implanted;

DETAILED DESCRIPTION OF PREFERRED EMBODIMENTS

Figure 6:
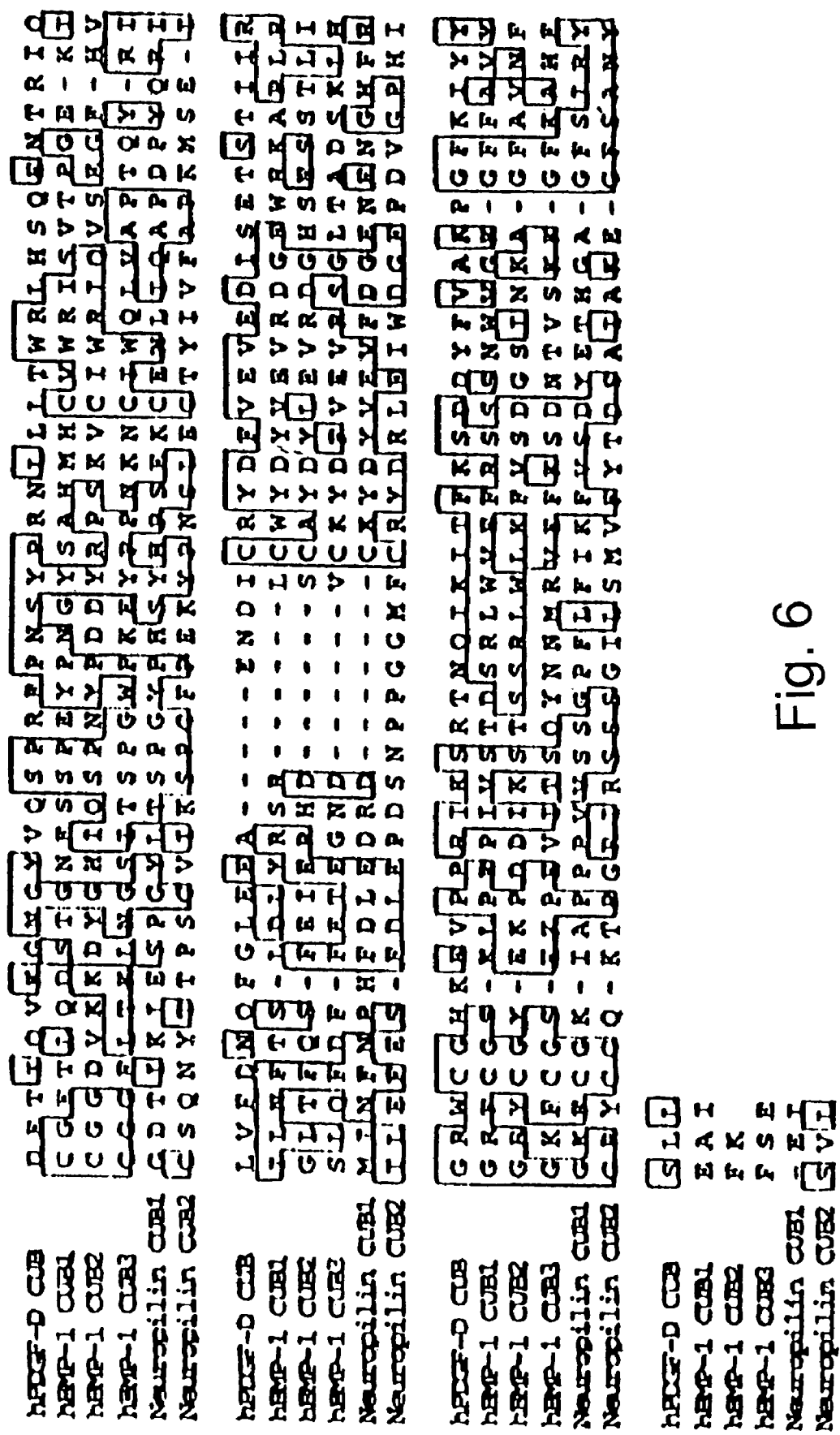
FIG. 6 shows an amino acid sequence alignment of the CUB domain present in HPDGF-D (SEQ ID NO:7) and other CUB domains present in human bone morphogenic protein-1 (hBMP-1, 3 CUB domains CUB1-3) (SEQ ID NOs:8-10, respectively) and in human neuropilin-1 (2 CUB domains) (SEQ ID NOs:11-12, respectively)

The present invention discloses a method of modulating, regulating and/or stabilizing angiogenesis in a mammal in need thereof, in which the PDGF-D level or activity or both in the mammal are modulated, preferably increased. In preferred embodiments, an active PDGF-D polypeptide in suitable amounts is directly administered to the mammal, or a polynucleotide encoding an active PDGF-D polypeptide is administered to the mammal, preferably at a location where angiogenesis modulating or stabilization is desired. Alternatively, endogenous expression of PDGF-D may be manipulated, either by increasing the expression level, or decreasing the degradation or clearing of expressed endogenous PDGF-D.

In a preferred embodiment, the PDGF-D is advantageously co-administered with an angiogenic growth factor, such as a member of the VEGF/PDGF family of growth factors, in particular VEGF-E.

The claimed method inhibits leakage of blood vessels and is useful, inter alia, for treatment of edemas. The known effects of increasing angiogenesis by, e.g. VEGF-E, and the angiogenesis stabilizing effects of PDGF-D, when combined according to the methods of the present invention, can be used for promoting wound healing as well as for other clinical treatment methods where angiogenesis promotion is desired.

Construction of PDGF-D Variants, Derivatives and Analogues

PDGF-D is a member of the PDGF family of growth factors which exhibits a high degree of homology to the other members of the PDGF family. PDGF-D contains seven conserved cysteine residues which are characteristic of this family of growth factors. These conserved cysteine residues form intra-chain disulfide bonds which produce the cysteine knot structure, and inter-chain disulfide bonds that form the protein dimers which are characteristic of members of the PDGF family of growth factors. PDGF-D interacts with a protein tyrosine kinase growth factor receptor.

In contrast to proteins where little or nothing is known about the protein structure and active sites needed for receptor binding and consequent activity, the design of active mutants of PDGF-D is greatly facilitated by the fact that a great deal is known about the active sites and important amino acids of the members of the PDGF family of growth factors.

Published articles elucidating the structure/activity relationships of members of the PDGF family of growth factors include for PDGF: Oestman et al., 1991, *J. Biol. Chem.*, 266:10073-10077; Andersson et al., 1992, *J. Biol. Chem.*, 267:11260-1266; Oefner et al., 1992, *EMBO J.*, 11:3921-3926; Flemming et al., 1993, *Molecular and Cell Biol.*, 13:4066-4076 and Andersson et al., 1995, *Growth Factors*, 12:159-164; and for VEGF: Kim et al., 1992, *Growth Factors*, 7:53-64; Pötgens et al., 1994, *J. Biol. Chem.*, 269:32879-32885 and Claffey et al., 1995, *Biochem. Biophys. Acta*, 1246: 1-9. From these publications it is apparent that because of the eight conserved cysteine residues, the members of the PDGF family of growth factors exhibit a characteristic knotted folding structure and dimerization, which result in formation of three exposed loop regions at each end of the dimerized molecule, at which the active receptor binding sites can be expected to be located.

Based on this information, a person skilled in the biotechnology arts can design PDGF-D mutants with a very high probability of retaining PDGF-D activity by conserving the eight cysteine residues responsible for the knotted folding arrangement and for dimerization, and also by conserving, or making only conservative amino acid substitutions in the likely receptor sequences in the loop 1, loop 2 and loop 3 region of the protein structure.

As used herein, the term "conservative substitution" denotes the replacement of an amino acid residue by another, biologically similar residue. Examples of conservative substitutions include the substitution of one hydrophobic residue such as isoleucine, valine, leucine, alanine, cysteine, glycine, phenylalanine, proline, tryptophan, tyrosine, norleucine or methionine for another, or the substitution of one polar residue for another, such as the substitution of arginine for lysine, glutamic acid for aspartic acid, or glutamine for asparagine, and the like. Neutral hydrophilic amino acids which can be substituted for one another include asparagine, glutamine, serine and threonine. The term "conservative substitution"

also includes the use of a substituted amino acid in place of an unsubstituted parent amino acid.

As such, it should be understood that in the context of the present invention, a conservative substitution is recognized in the art as a substitution of one amino acid for another amino acid that has similar properties. Exemplary conservative substitutions are set out in the following Table A from WO 97/09433.

TABLE A

Conservative Substitutions I

| SIDE CHAIN CHARACTERISTIC | AMINO ACID |
|---|---|
| Aliphatic | |
| Non-polar | G A P I L V |
| Polar - uncharged | C S T M N Q |
| Polar - charged | D E K R |
| Aromatic | H F W Y |
| Other | N Q D E |

Alternatively, conservative amino acids can be grouped as described in Lehninger, Biochemistry, Second Edition; Worth Publishers, Inc. NY:N.Y. (1975), pp. 71-77 as set out in the following Table B.

TABLE B

Conservative Substitutions II

| SIDE CHAIN CHARACTERISTIC | AMINO ACID |
|---|---|
| Non-polar (hydrophobic) | |
| A. Aliphatic: | A L I V P |
| B. Aromatic: | F W |
| C. Sulfur-containing: | M |
| D. Borderline: | G |
| Uncharged-polar | |
| A. Hydroxyl: | S T Y |
| B. Amides: | N Q |
| C. Sulfhydryl: | C |
| D. Borderline: | G |
| Positively Charged (Basic): | K R H |
| Negatively Charged (Acidic): | D E |

Exemplary conservative substitutions are set out in the following Table C.

TABLE C

Conservative Substitutions III

| Original Residue | Exemplary Substitution |
|---|---|
| Ala (A) | Val, Leu, Ile |
| Arg (R) | Lys, Gln, Asn |
| Asn (N) | Gln, His, Lys, Arg |
| Asp (D) | Glu |
| Cys (C) | Ser |

TABLE C-continued

Conservative Substitutions III

| Original Residue | Exemplary Substitution |
|---|---|
| Gln (Q) | Asn |
| Glu (E) | Asp |
| His (H) | Asn, Gln, Lys, Arg |
| Ile (I) | Leu, Val, Met, Ala, Phe, |
| Leu (L) | Ile, Val, Met, Ala, Phe |
| Lys (K) | Arg, Gln, Asn |
| Met (M) | Leu, Phe, Ile |
| Phe (F) | Leu, Val, Ile, Ala |
| Pro (P) | Gly |
| Ser (S) | Thr |
| Thr (T) | Ser |
| Trp (W) | Tyr, Phe |
| Tyr (Y) | Trp, Phe, Thr, Ser |
| Val (V) | Ile, Leu, Met, Phe, Ala |

If desired, the peptides of the invention can be modified, for instance, by glycosylation, amidation, carboxylation, or phosphorylation, or by the creation of acid addition salts, amides, esters, in particular C-terminal esters, and N-acyl derivatives of the peptides of the invention. The peptides also can be modified to create peptide derivatives by forming covalent or noncovalent complexes with other moieties. Covalently-bound complexes can be prepared by linking the chemical moieties to functional groups on the side chains of amino acids comprising the peptides, or at the N- or C-terminus.

The formation of desired mutations at specifically targeted sites in a protein structure is considered to be a standard technique in the arsenal of the protein chemist (Kunkel et al., 1987, *Methods in Enzymol*. 154:367-382). Examples of such site-directed mutagenesis with VEGF can be found in Pötgens et al., 1994, *J. Biol. Chem.* 269:32879-32885 and Claffey et al., 1995, *Biochem. Biophys. Acta*, 1246:1-9. Indeed, site-directed mutagenesis is so common that kits are commercially available to facilitate such procedures (e.g. Promega 1994-1995 Catalog., Pages 142-145).

PDGF-D derivatives, variants and analogs of the present invention further include polypeptides that are at least 70% or at least 80% identical to SEQ ID NO:2, SEQ ID NO: 3 (the 200 amino acids set out in FIG. 3) or SEQ ID NO: 4 (the 322 amino acid sequence set out in FIG. 4 (SEQ ID NO:4), or amino acids 254-370 of FIG. 1 which is the PVDH domain.

In this regard, polypeptides at least 90% identical to the same are particularly preferred, and among these particularly preferred polynucleotides, those with at least 95% are especially preferred. Furthermore, those with at least 97% are highly preferred among those with at least 95%, and among these those with at least 98% and at least 99% are particularly highly preferred, with at least 99% being the more preferred.

PDGF-D derivatives, variants and analogs of the present invention further include polynucleotides encoding the polypeptides described above.

The activity, especially the angiogenesis modulating, regulating and/or stabilizing activity, PDGF-D mutants can be readily confirmed by well-established routine screening procedures using methods which are well known in the art.

FIG. 1 shows the amino acid sequence of full-length hPDGF-D containing 370 amino acid residues (SEQ ID NO:2). FIG. 2 (SEQ ID NO:1) shows the 1116 bp polynucleotide sequence of a cDNA encoding full-length hPDGF-D.

PDGF-D has a two-domain structure with a N-terminal CUB domain (residues 67-167, discussed below) and a C-terminal PDGF/VEGF homology domain. The homology domain, alternatively known as the core domain, can be as long as residues 254-370, or as short as residues 272-362, and includes any intermediate fragment in between. The overall amino acid sequence identity between PDGF-C (SEQ ID NO:6) and PDGF-D (SEQ ID NO:2) is approximately 43% (FIG. 5). The similarities are highest in the distinct protein domains while the N-terminal region, including the hydrophobic signal sequence, and the hinge region between the two domains display lower identities. A putative signal peptidase cleavage site was identified between residues 22-23. Cleavage results in a protein of 348 residues with a calculated molecular mass ($M_r$) of 44,000. A single putative site for N-linked glycosylation was identified in the core domain of PDGF-D (residues 276-278).

With two exceptions, PDGF-D has the expected pattern of invariant cysteine residues, involved in inter- and intra-disulfide bonding, a hallmark of members of this family. The first exception occurs between cysteine 3 and 4. Normally these two cysteines are spaced by 2 residues. However, similar to PDGF-C, PDGF-D has an unique insertion of three additional amino acids residues, NCG. In total, ten cysteine residues reside in the core domain, including the extreme C-terminal region, suggesting a unique arrangement of the cysteines in the disulfide-bonded PDGF-D dimer. The second exception is that the invariant fifth cysteine found in the other members of the PDGF/VEGF family is not conserved in PDGF-D. This feature is unique to PDGF-D.

The N-terminal region of the partial PDGF-D amino acid sequence of FIG. 6 (residues 53-170 of SEQ ID NO:2) has a second distinct protein domain which is referred to as a CUB domain (Bork and Beckmann, 1993, *J. Mol. Biol.* 231:539-545). This domain of about 115 amino acids was originally identified in complement factors C1/C1s, but has recently been identified in several other extracellular proteins including signaling molecules such as bone morphogenic protein 1 (BMP-1) (Wozney et al., 1988, *Science*, 242:1528-1534) as well as in several receptor molecules such as neuropilin-1 (NP-1) (Soker et al., 1998, *Cell* 92:735-745). The functional roles of CUB domains are not clear but they may participate in protein-protein interactions or in interactions with carbohydrates including heparin sulfate proteoglycans. These interactions may play a role in the proteolytic activation of PDGF-D.

PDGF-DD is a PDGFR-beta-specific agonist. Proteolytic processing of PDGF-DD releases the core domains from the N-terminal CUB domains which is necessary for unmasking the receptor-binding epitopes of the core domain similar to the situation for PDGF-CC.

Murine PDGF-D sequences have been determined. A second mouse clone was almost identical to an earlier mouse sequence identified, however, it lacked six amino acid residues (aa 42-47) from the region between the signal sequence and the CUB domain.

Figure 7A:
FIG. 7A shows a schematic representation of the PDGF-D sequence.
Figure 7B:
FIG. 7B shows a schematic representation of the PDGF-D sequence variant, which corresponds to FIG. 7A but for 6 missing amino acid residues.
Figure 7C:
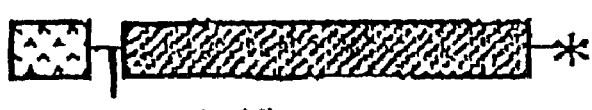
FIG. 7C shows a schematic representation of the PDGF-D sequence variant, which corresponds to FIG. 7A but for 6 missing amino acid residues and the loss of the PDGF homology domain in this sequence variant.

A third mouse clone was also obtained which comprised of part of the earlier mouse sequence, lacking amino acids 42-47 as in the second clone, and also lacking the PDGF-homology domain. The similarities and differences between regions of the three clones are depicted in FIG. 7.

The surprising results show that at least two alternatively spliced versions of the PDGF-D gene are transcribed into polyadenylated RNA. The variant transcript structures suggest an alternative splice acceptor site is used in exon two, producing a variant protein lacking six amino acid residues (ESNHLT).

In addition to lacking the above noted six amino acid residues, the third clone also lacks the PDGF-homology domain. This is because of the skipping of exon six and the resulting frame shift. This ends the open reading frame in a stop codon after four additional amino acid residues (GIEV). As shown in detail in FIG. 8, this splice variant only contains the amino terminal CUB domain and could potentially provide an inhibitor of PDGF-D functions. The potential inhibition function is because the activation of full-length PDGF-D binding to the PDGFR-D requires proteolytic removal of the CUB domain.

EXAMPLES

Example 1

Generation of Recombinant Human PDGF-DD Core Domain

Figure 9:
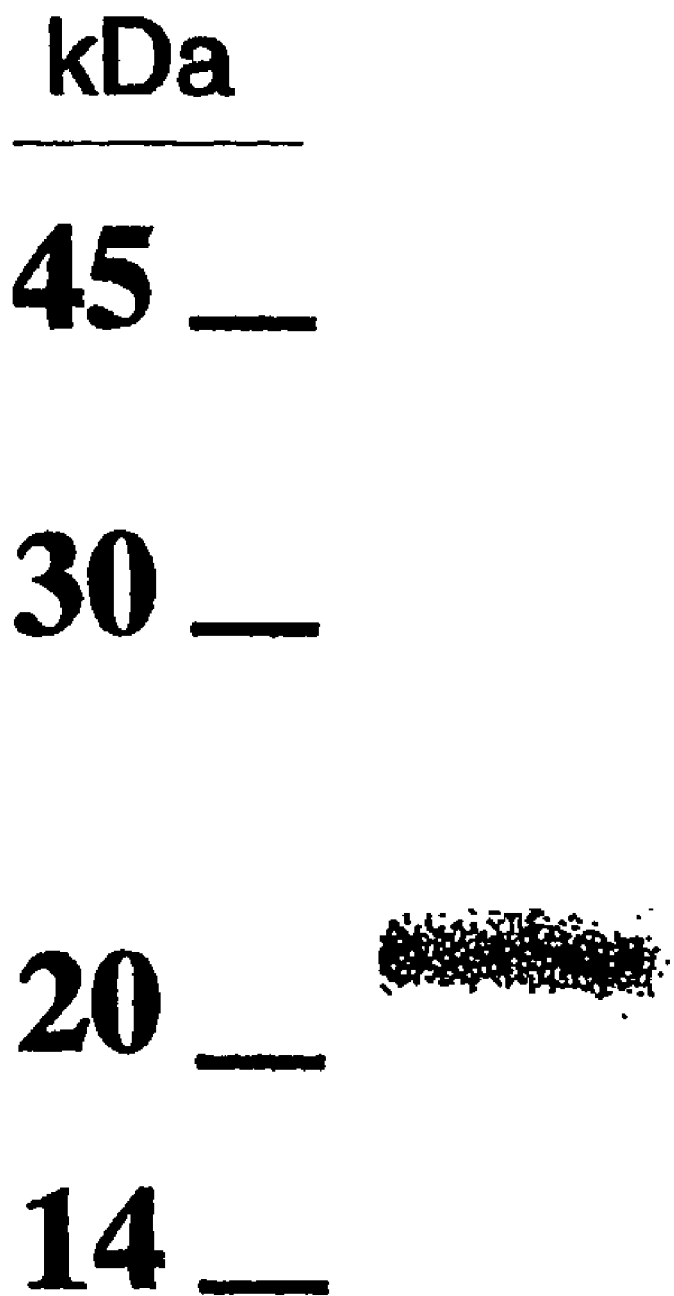
FIG. 9 shows an SDS-PAGE analysis under reducing conditions of human PDGF-DD formed from the core domain of factor Xa-digested mutant full-length form of PDGF-D.
Figure 11:
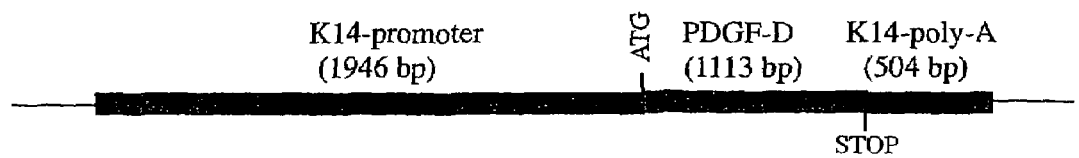
FIG. 11 is a schematic diagram showing a K14-PDGF-D construct.
Figure 12:
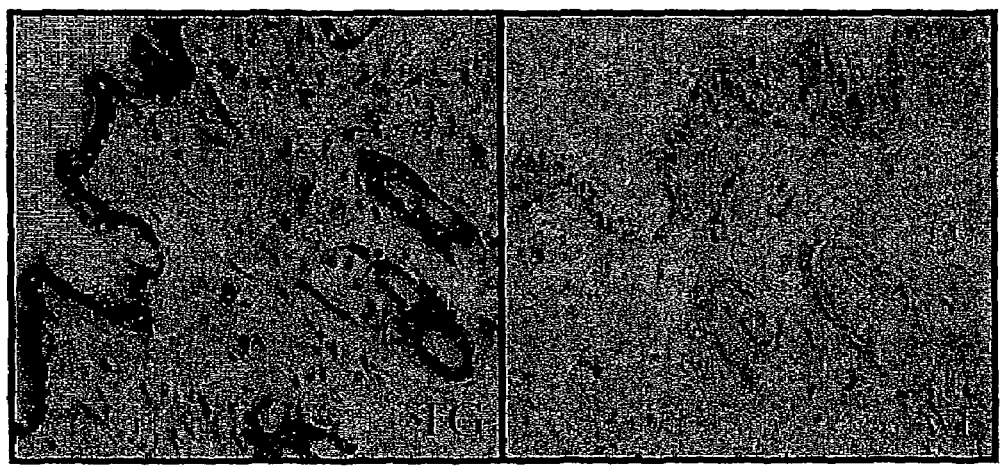
FIG. 12 shows a comparison of PDGF-D expression between K14-PDGF-D transgenic mouse (TG) and wild-type mouse (wt). Paraffin embedded mouse skin samples were stained with anti-PDGF-D. For experimental details, see Uutela et al., 2001, "Chromosomal location, exon structure and vascular expression patterns of the human PDGF-C and PDGF-D genes," Circulation 103:2242-2247.

The process as described (Bergsten et al., 2001, *Nat. Cell Biol.* 3:512-516) was followed to generate recombinant human PDGF-DD core domain. Human PDGF-DD was expressed as a mutant full-length form containing a factor Xa protease cleavage site. Amino acids 251-258 were replaced with 2 tandem factor Xa cleavage sites of Ile Glu Gly Arg (residues 1-4 of SEQ ID NO: 5) (i.e. Ile Glu Gly Arg Ile Glu Gly Arg; SEQ ID NO: 5) that allowed the generation of the active C-terminal fragment of the protein (PDGF-homology domain) upon cleavage with factor Xa. The recombinant protein has an extreme C-terminal $His_6$-tag (SEQ ID NO: 16) to allow its purification on a nickel-containing resin. Following purification, the protein solution was dialyzed against 0.1M acetic acid and lyophilized. SDS-PAGE analysis under reducing conditions on the purified protein revealed that it migrated as a homogenous 21 kDa species (see FIG. 9). The purified protein was lyophilized for storage.

Example 2

Comparison of Angiogenic Activities of the Human PDGF-DD Core Domain with Other PDGF Isoforms The mouse corneal micropocket assay was performed according to procedures described in Cao et al., 1998, *Proc Nat'l. Acad. Sci USA* 95:14389-94; Cao et al., 1999, *Nature* 398:381. Specifically, lyophilized proteins were dissolved in phosphate buffer solutions (PBS) and used to make protein bound polymer beads, as described.

The beads were then implanted in mouse cornea. Male 5-6 week-old C57Bl6/J mice were acclimated and caged in groups of six or less. Animals were anaesthetized by injection of a mixture of dormicum and hypnorm (1:1) before all procedures. Corneal micropockets were created with a modified von Graefe cataract knife in both eyes of each male 5-6-week-old C57Bl6/J mouse. A micropellet (0.35×0.35 mm) of sucrose aluminum sulfate (Bukh Meditec, Copenhagen, Denmark) coated with slow-release hydron polymer type NCC (IFN Sciences, New Brunswick, N.J.) containing various amounts of homodimers of truncated PDGF-DD was surgically implanted into each corneal pocket.

For comparison purposes corresponding amounts of PDGF-AA, PDGF-AB, PDGF-BB, and PDGF-CC were similarly implanted into corneal pockets of test mice. In each case, the pellet was positioned 0.6-0.8 mm from the corneal limbus. After implantation, erythromycin/ophthalmic ointment was applied to each eye.

On day 5 after growth factor implantation, animals were sacrificed with a lethal dose of $CO_2$, and corneal neovascularization was measured and photographed with a slit-lamp stereomicroscope. In FIGS. 10A-E, arrows point to the implanted pellets. Vessel length and clock hours of circumferential neovascularization were measured. Quantitation of corneal neovascularization is presented as maximal vessel length (FIG. 10F), clock hours of circumferential neovascularization (FIG. 10G), and area of neovascularization (FIG. 10H). Graphs represent mean values (Å SEM) of 11-16 eyes (6-8 mice) in each group.

The corneal angiogenesis model is one of the most rigorous mammalian angiogenesis models that requires a putative compound to be sufficiently potent in order to induce neovascularization in the corneal avascular tissue. Potent angiogenic factors including FGF-2 and VEGF have profound effects in this system.

The results are shown in FIG. 10. The assays were done using PDGF-AA (FIG. 10A), PDGF-AB (FIG. 10B), PDGF-BB (FIG. 10C), PDGF-CC (FIG. 10D), and PDGF-DD (FIG. 10C). FIGS. 10F-H show the quantitative analysis of vessel length, clock hours, and vessel areas (means±SD, n=4-6).

The overall angiogenic response induced by PDGF-DD was similar to that induced by other PDGF isoforms. The results again clearly demonstrate that the truncated PDGF-D homodimer exhibits marked angiogenic activity in vivo. In light of the foregoing test results, which demonstrate the in vivo angiogenesis inducing activity of PDGF-DD, treatments with PDGF-DD alone, or in combination with other angiogenic factors such as VEGF family members and FGFs, provide an attractive approach for therapeutic angiogenesis of ischemic heart, brain and limb disorders.

Example 3

Generation and Analysis of K14-PDGF-D Transgenic Mice

Human PDGF-D cDNA (bp 176-1285; GenBank seq. number: AF336376) was inserted into the Bam HI site of the K14 promoter expression vector [Vassar et al., 1989, *Proc. Natl. Acad. Sci. USA* 86:1563-1567]. This directs expression of the gene to the basal epithelial cells of the skin of transgenic animals (Jeltsch et al. 1997 Hyperplasia of lymphatic vessels in VEGF-C transgenic mice. Science 276:1423-1425). FIG. 13A shows a schematic diagram of the resulting K14-PDGF-D construct. The construct was digested with EcoRI and SphI and the expression cassette was purified. A 5 ng/μl solution of the DNA was injected into fertilized eggs of the FVB-strain of mice and the resulting transgenic mice were maintained in this strain. To analyze the transgene expression, PDGF mRNA expression in the skin of transgenic and wild type littermate mice was studied. Tissues were snap-frozen in liquid nitrogen and homogenized with a dismembrator. Total RNA was extracted with the RNEasy Kit (QIAGEN GmbH). 10-20 μg of total RNA was electrophoresed in 1% agarose and transferred to a nylon membrane (Nytran, Schleicher & Schuell), which was then hybridized with a human PDGF-D probe (bp 119 to 1268) and subjected to autoradiography. Protein expression was verified by immunohistochemistry using anti-PDGF-D antibodies [Uutela et al., 2001, *Circulation* 103:2242-2247]. Two transgenic lines were used for the analysis.

Figure 13:
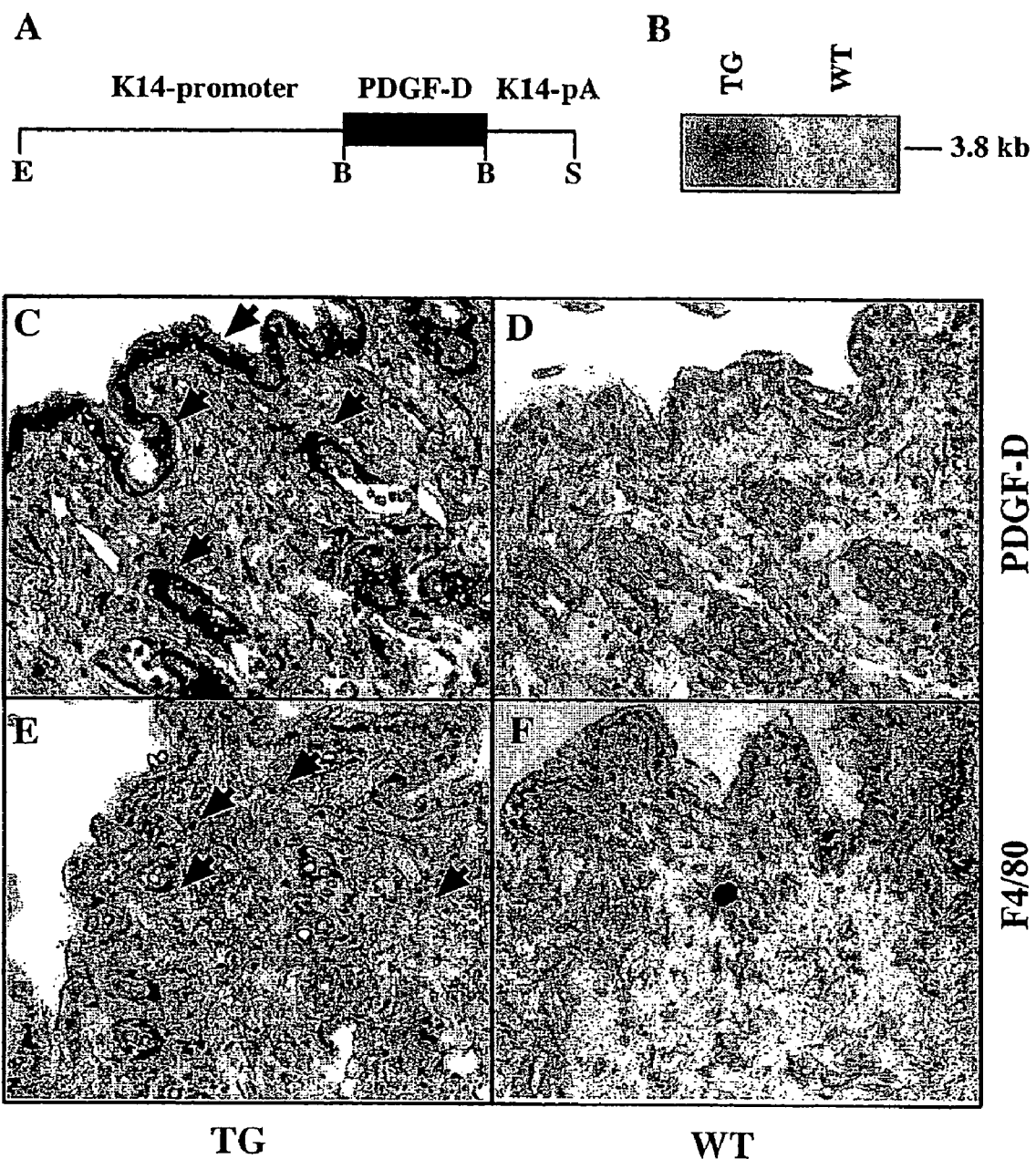
FIGS. 13A-F show the K14-PDGF-D transgene, its mRNA expression, expression of the transgene in the skin, and analysis of the phenotype in the dermis of transgenic mice.
Figure 14:
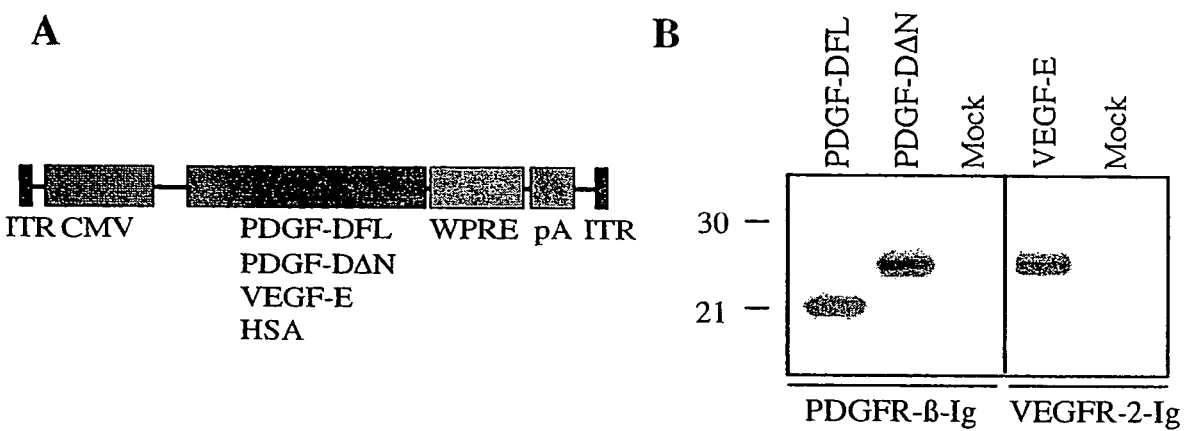
FIGS. 14A and B show a schematic presentation of an AAV-PDGF-D construct and an in vitro expression analysis of AAV infected HeLa cells.
Figure 15:
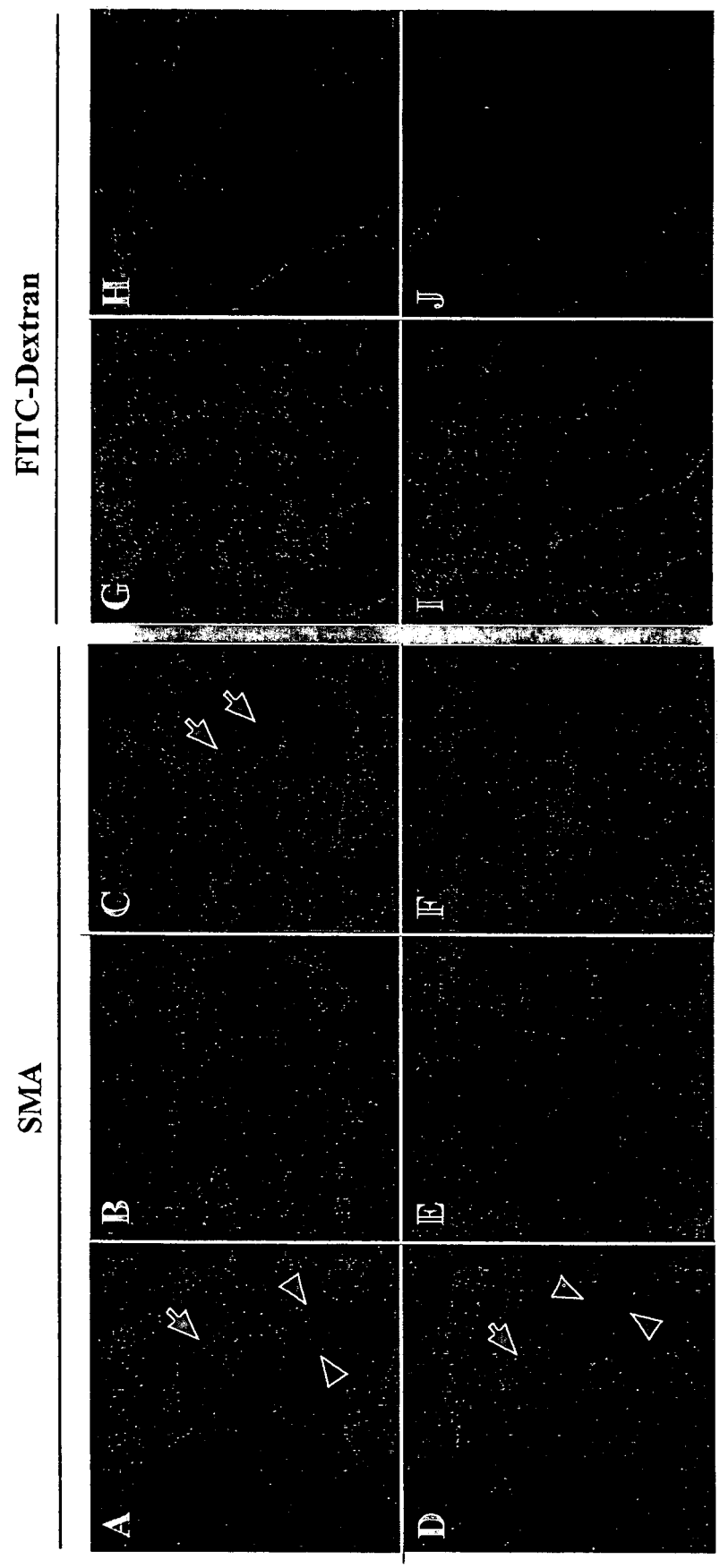
FIGS. 15A-J show that AAV-PDGF-D infection of mouse ears stabilizes and reduces leakage of blood vessels induced by VEGF-E.

PDGF-D expression was detected in the skin of the transgenic, but not control littermate mice by Northern hybridization and immunohistochemistry. FIG. 13B is a Northern blot of skin total RNA hybridized with radioactive PDGF-D probe showing the mRNA product of the transgene construct. Equal loading of the first two lanes was confirmed by ethidium bromide staining of RNA. FIGS. 13C through 31F show immunostaining of the skin. Using parafiin-embedded mouse skin samples, an anti-PDGF-D antibody was shown to stain the basal keratinocytes in K14-PDGF-D skin (FIG. 13C, arrowheads) but not in wild type littermate skin (FIG. 13D). A Rat anti-mouse monoclonal antibody which detects macrophages (Serotec) was used to stain for F4/80 which detects macrophages. Very strong staining in the transgenic mouse skin (FIG. 13E, arrowheads) was seen when compared to wild type littermate skin (FIG. 13F).

Example 4

Generation of AAV Expression Vectors

In order to analyze the effects of PDGF-D expression in adult skin and muscle, AAV vectors encoding the full-length PDGF-D (DFL) or the activated form (ΔN) lacking the CUB domain were generated and tested in vitro. AAV encoding HSA was used as a control. VEGF-E was also cloned into AAV. FIG. 14B shows an in vitro expression analysis of AAV infected HeLa cells. The PDGFs were precipitated with PDGFR-β-Ig and VEGF-E with VEGFR-2-Ig.

The full length VEGF-E (bp 1-399, GenBank seq. AF106020), the full length PDGF-D (PDGF-DFL), and a short form (PDGF-DΔN, bp 917-1285) as well as human serum albumin (HSA, bp 112-1866, GenBank seq. NM_000477) cDNAs were cloned as blunt-end fragments into the MluI site of the psub-CMV-WPRE plasmid [Paterna et al., 2000, *Gene Ther.* 7:1304-1311]. FIG. 14A is a schematic presentation of the AAV-PDGF-D constructs. The human PDGF-DFL, PDGF-DΔN, VEGF-E and HSA cDNAs are driven by the CMV promoter and early enhancer (CMV), promoted by the Woodchuck post-transcriptional enhancer-element (WPRE). pA is the SV40 polyadenylation signal. The recombinant AAVs were produced as described in Karkkainen et al., 2001, A model for gene therapy of human hereditary lymphedema, *Proc. Nat'l. Acad. Sci. USA* 98:12677-12682. 50 μl of purified AAV ($5\times10^{11}$ genomic particles/ml) was injected into mouse ear or gastrognemius muscle and four weeks later the mice were sacrificed and the tissues analyzed.

To construct a VEGFR-2/IgG expression plasmid, the first three Ig homology domains of the extracellular part of VEGFR-2 were amplified by PCR using primers 5'-GCG-GATCCTTGCCTAGTGTTTCTCTTGATC-3' (SEQ ID NO:13) and 5'-CCAGTCACCTGCTCCGGATCTTCATG-GACCCTGACAAATG-3' (SEQ ID NO:14) and cloned into the Signal pIgplus vector (Ingenius). The resulting plasmid was cut with BamHI and KpnI, treated with T4 polymerase and back-ligated. The generation of stable Drosophila S2 cells and purification of the VEGFR-2-Ig fusion proteins was carried out as described by Makinen et al., 2001, Inhibition of lymphangiogenesis with resulting lymphedema in transgenic mice expressing soluble VEGF receptor-3, *Nat Med.* 7:199-205.

HeLa cells were infected with 2 μl purified AAV ($5 \times 10^{11}$ genomic particles/ml) in 5 ml DMEM supplemented with 2% fetal bovine serum and glutamine overnight, after which the cells were washed and cultured for further 24 hours in DMEM supplemented with 10% fetal bovine serum and glutamine. The cells were metabolically labeled in methionine and cysteine free MEM supplemented with 100 μCi/ml [$^{35}$S] methionine and [$^{35}$S] cysteine (Redivue ProMix; Amersham Pharmacia Biotech). Immunoprecipitation of metabolically $^{35}$S-labeled PDGF-D was carried out by using PDGFR-α-Ig or PDGFR-β-Ig (R&D), and VEGF-E was precipitated by a VEGF receptor 2-Ig. The complexes were adsorbed to protein A-sepharose (Pharmacia), washed twice in 0.5% BSA, 0.02% Tween 20 in PBS, and once in PBS and analyzed in a 12.5% SDS-PAGE under reducing conditions.

Example 5

Stabilization of VEGF-E Induced Blood Vessels by PDGF-D

PDGF-B has been implicated in the stabilization of blood vessels during angiogenesis [Saharinen et al., 2003, Double target for tumor mass destruction. *J. Clin. Invest.* 111:1277-1280]. To investigate the possible contribution to angiogenic responses, AAV-PDGF-D was tested, alone in combination with AAV producing the angiogenic factor VEGF-E, in the ears of 4-6 week old mice. In addition, transgenic mice expressing K14-PDGF-D or K14-VEGF-E were also compared with transgenic mice that express both K14-PDGF-D and K14-VEGF-E.

a. AAV Infection Experiments

AAV-PDGF-D and AAV-VEGF-E, alone or in combination, were used to infect ears of 4-6 weeks mice, and the blood vessels of the ears were examined using the FITC-Dextran staining as described by Fukumura et al., 1995, Tumor necrosis factor α-induced leucocyte adhesion in normal and tumor vessel: effect of tumor type, transplantation site, and host strain, *Cancer Res.* 55:4824-4829. Briefly, mice were anesthetized and 200 μl FITC-Dextran (2000 kDa, 20 mg/ml in phosphate-buffered solution) was injected intravenously into the tail vein through a 30G needle. The ears were monitored under a fluorescence microscope, and equal length exposed pictures were taken after 1, 2 and 4 minutes. Fluorescent microangiography was performed as described by Saaristo et al., 2002, Lymphangiogenic gene therapy with minimal blood vascular side effects, *J. Exp. Med.* 196:719-730.

Whole mount staining of smooth muscle actin (SMA) positive blood vessels was performed by first fixing the ears with 4% paraformaldehyde, after this, tissues were blocked in 3% milk 0.3% Triton-X in PBS overnight and Cy$^3$ conjugated antibodies against SMA (Sigma) were applied overnight at +4° C. and viewed in a Zeiss Axioplan 2 fluorescent microscope.

AAV-VEGF-E was found to induce a strong angiogenic response detected in whole mount ears stained for the PECAM-1 and SMA. Vessels were increased in diameter (see arrowheads in FIG. 15A) in comparison to AAV-HSV (FIG. 15B). The AAV-VEGF-E infected ears stained for SMA showed a loose, irregular coating by smooth muscle cells (FIGS. 15A and 15C) in comparison with AAV-HSA infected ears. Interestingly, the ears injected with the combination of AAV-PDGF-D and AAV-VEGF-E, showed a normal tight structure of the smooth muscle layer (FIGS. 15D and 15F), similar to the AAV-HSA or AAV-PDGF-D injected ears (FIGS. 15B and 15E) and the vessels had an increased diameter. When tested for vascular leakiness by injecting FITC-Dextran into the tail vein, the vessels in the ears treated with the combination of AAV-PDGF-D and AAV-VEGF-E had clearly reduced leakiness (FIG. 15I) in comparison with the vessels formed in the ears injected with AAV-VEGF-E only (FIG. 15G). In contrast, the VEGF-E induced increase of blood capillaries was unaffected and AAV-PDGF-D alone did not seem to have an effect on the smooth muscle cell coating or leakiness of the vessels (FIG. 15J).

When the angiogenic effects of PDGF-D gene transduction in the ear and skeletal muscle were tested, PDGF-D alone was not angiogenic. But when PDGF-D was expressed together with VEGF-E, which has been shown to induce a strong angiogenic response [Kiba et al., 2003, VEGFR-2-specific ligand VEGF-E induces non-edematous hyper-vascularization in mice. *Biochem. Biophys. Res. Commun.* 301:371-377], PDGF-D was found to stabilize newly generated, enlarged and leaky vessels induced by VEGF-E alone. This effect may due to the PDGF-D induced stimulation of the proliferation and migration of smooth muscle cells (SMCs), as has been shown for coronary artery SMCs in vitro [Jutela et al., 2001, Chromosomal Location, Exon Structure and Vascular Expression Patterns of the Human PDGF-C and PDGF-D Genes. *Circulation* 103:2242-2247]. Consistent with such a possibility, the whole mount staining for smooth muscle actin indicated that the vessels induced by VEGF-E have an abnormally sparse SMC coating, but when combined with PDGF-D, the SMC layer seemed comparable to that in the untreated skin. This indicates that PDGF-D can play an important role in stabilizing newly formed vessels by recruiting SMCs.

b. Transgenic Mice Experiment

Figure 16:
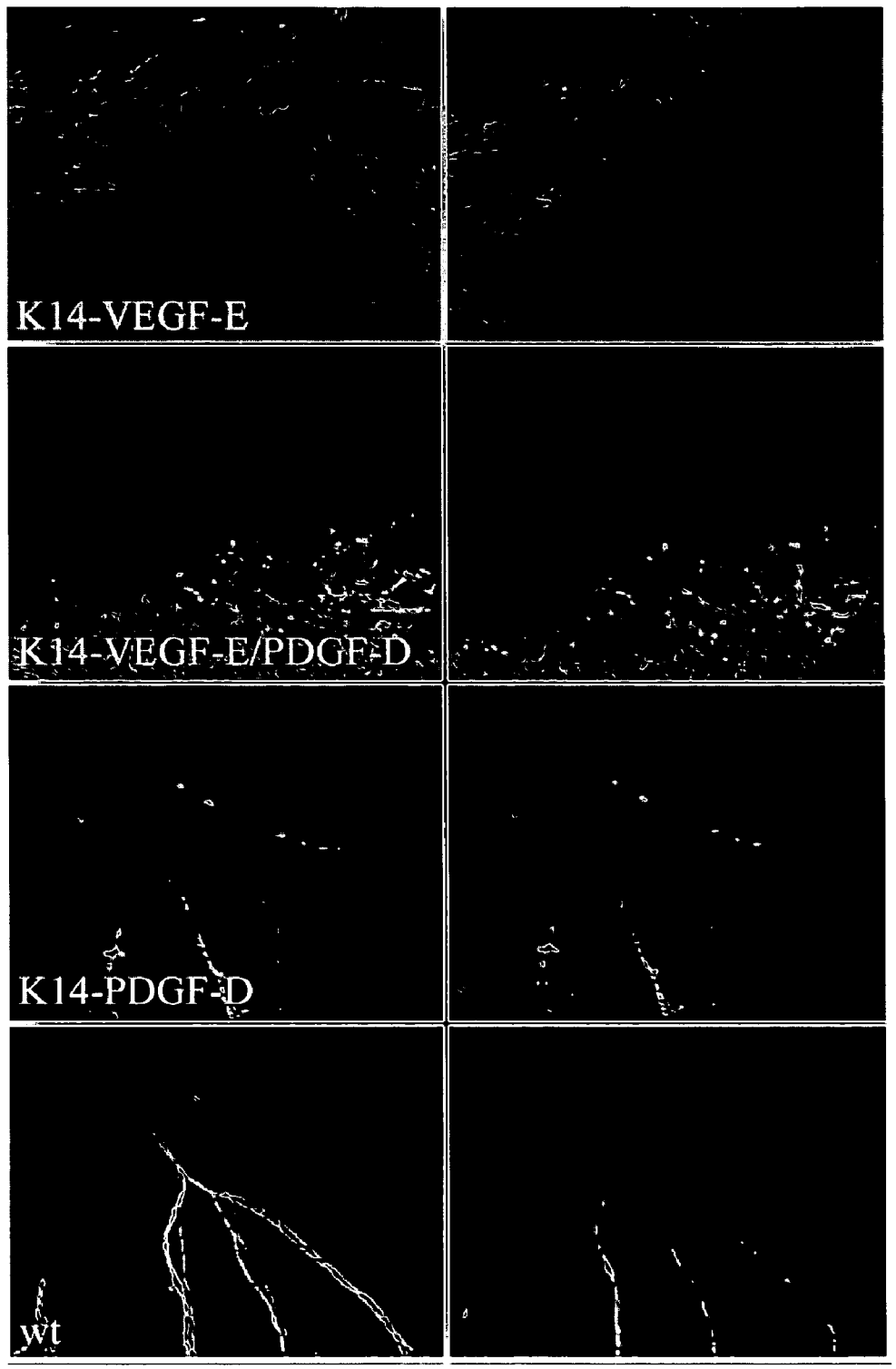
FIG. 16 shows that transgenic mice expressing both PDGF-D and VEGF-E had significantly less blood vessel leakage as compared to transgenic mice expressing VEGF-E alone.

K14-PDGF-D transgenic mice were generated and examined as described in Example 3, supra. Transgenic mice expressing K14-VEGF-E were obtained courtesy of Shibuya and were previously published (Kiba et al., (2003) VEGFR-2-specific ligand VEGF-E induces non-edematous hyper-vascularization in mice. Biochem. Biophys. Res. Commun., 301:371-377). K14-PDGF-D mice were mated with K14-VEGF-E mice, and progeny expressing both PDGF-D and VEGF-E were selected. FITC-Dextran staining on PDGF-D, VEGF-E and PDGF-D/VEGF-E, as well as wild-type mice were performed as described above. The results are shown in FIG. 16. The results demonstrate that blood vessels in the VEGF-E transgenic mice showed significant leakage, while the PDGF-D transgenic mice were virtually indistinguishable from the wild-type mice. Significantly, in the mice expressing both VEGF-E and PDGF-D, the leakage induced by VEGF-E was reduced.

The foregoing description and examples have been set forth merely to illustrate the invention and are not intended to be limiting. Since modifications of the disclosed embodiments incorporating the spirit and substance of the invention may occur to persons skilled in the art, the invention should be construed broadly to include all variations falling within the scope of the appended claims and equivalents thereof. All references cited hereinabove and/or listed below are hereby expressly incorporated by reference.

What is claimed is:

1. A method for modulating, regulating or stabilizing angiogenesis in a mammal comprising administering an amount of truncated, homodimeric PDGF-DD, wherein each truncated monomer consists of amino acids 259-370 of SEQ ID NO; 2 to a mammal in need of modulation, regulation or stabilization of angiogenesis.

2. The method of claim 1, farther comprising administering a growth factor from he VEGF/PDGF family.

3. The method of claim 2, wherein said growth factor is VEGF-E.

4. The method of claim 2, further comprising administering VEGF-A.

5. The method of claim 1, wherein said mammal is a human.

6. The method of claim 1, comprising administering said truncated homodimeric, PDGF-DD with a pharmaceutically acceptable carrier.

* * * * *

SEQUENCE LISTING

<160> NUMBER OF SEQ ID NOS: 16

<210> SEQ ID NO 1
<211> LENGTH: 2253
<212> TYPE: DNA
<213> ORGANISM: Homo sapiens
<220> FEATURE:
<221> NAME/KEY: CDS
<222> LOCATION: (176)..(1285)

<400> SEQUENCE: 1

```
cgctcggaaa gttcagcatg caggaagttt ggggagagct cggcgattag cacagcgacc      60
cgggccagcg cagggcgagc gcaggcggcg agagcgcagg gcggcgcggc gtcggtcccg     120
ggagcagaac ccggcttttt cttggagcga cgctgtctct agtcgctgat cccaa atg     178
                                                              Met
                                                               1 cac cgg ctc atc ttt gtc tac act cta atc tgc gca aac ttt tgc agc      226
His Arg Leu Ile Phe Val Tyr Thr Leu Ile Cys Ala Asn Phe Cys Ser
            5                  10                  15 tgt cgg gac act tct gca acc ccg cag agc gca tcc atc aaa gct ttg      274
Cys Arg Asp Thr Ser Ala Thr Pro Gln Ser Ala Ser Ile Lys Ala Leu
         20                  25                  30 cgc aac gcc aac ctc agg cga gat gag agc aat cac ctc aca gac ttg      322
Arg Asn Ala Asn Leu Arg Arg Asp Glu Ser Asn His Leu Thr Asp Leu
     35                  40                  45 tac cga aga gat gag acc atc cag gtg aaa gga aac ggc tac gtg cag      370
Tyr Arg Arg Asp Glu Thr Ile Gln Val Lys Gly Asn Gly Tyr Val Gln
 50                  55                  60                  65 agt cct aga ttc ccg aac agc tac ccc agg aac ctg ctc ctg aca tgg      418
Ser Pro Arg Phe Pro Asn Ser Tyr Pro Arg Asn Leu Leu Leu Thr Trp
                 70                  75                  80 cgg ctt cac tct cag gag aat aca cgg ata cag cta gtg ttt gac aat      466
Arg Leu His Ser Gln Glu Asn Thr Arg Ile Gln Leu Val Phe Asp Asn
             85                  90                  95 cag ttt gga tta gag gaa gca gaa aat gat atc tgt agg tat gat ttt      514
Gln Phe Gly Leu Glu Glu Ala Glu Asn Asp Ile Cys Arg Tyr Asp Phe
        100                 105                 110 gtg gaa gtt gaa gat ata tcc gaa acc agt acc att att aga gga cga      562
Val Glu Val Glu Asp Ile Ser Glu Thr Ser Thr Ile Ile Arg Gly Arg
    115                 120                 125 tgg tgt gga cac aag gaa gtt cct cca agg ata aaa tca aga acg aac      610
Trp Cys Gly His Lys Glu Val Pro Pro Arg Ile Lys Ser Arg Thr Asn
130                 135                 140                 145 caa att aaa atc aca ttc aag tcc gat gac tac ttt gtg gct aaa cct      658
Gln Ile Lys Ile Thr Phe Lys Ser Asp Asp Tyr Phe Val Ala Lys Pro
                150                 155                 160 gga ttc aag att tat tat tct ttg ctg gaa gat ttc caa ccc gca gca      706
Gly Phe Lys Ile Tyr Tyr Ser Leu Leu Glu Asp Phe Gln Pro Ala Ala
            165                 170                 175 gct tca gag acc aac tgg gaa tct gtc aca agc tct att tca ggg gta      754
Ala Ser Glu Thr Asn Trp Glu Ser Val Thr Ser Ser Ile Ser Gly Val
        180                 185                 190 tcc tat aac tct cca tca gta acg gat ccc act ctg att gcg gat gct      802
Ser Tyr Asn Ser Pro Ser Val Thr Asp Pro Thr Leu Ile Ala Asp Ala
    195                 200                 205 ctg gac aaa aaa att gca gaa ttt gat aca gtg gaa gat ctc ctc aag      850
Leu Asp Lys Lys Ile Ala Glu Phe Asp Thr Val Glu Asp Leu Leu Lys
210                 215                 220                 225
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| tac | ttc | aat | cca | gag | tca | tgg | caa | gaa | gat | ctt | gag | aat | atg | tat | ctg | 898  |
| Tyr | Phe | Asn | Pro | Glu | Ser | Trp | Gln | Glu | Asp | Leu | Glu | Asn | Met | Tyr | Leu |      |
|     |     |     |     | 230 |     |     |     |     | 235 |     |     |     |     | 240 |     |      |
| gac | acc | cct | cgg | tat | cga | ggc | agg | tca | tac | cat | gac | cgg | aag | tca | aaa | 946  |
| Asp | Thr | Pro | Arg | Tyr | Arg | Gly | Arg | Ser | Tyr | His | Asp | Arg | Lys | Ser | Lys |      |
|     |     | 245 |     |     |     |     | 250 |     |     |     |     | 255 |     |     |     |      |
| gtt | gac | ctg | gat | agg | ctc | aat | gat | gat | gcc | aag | cgt | tac | agt | tgc | act | 994  |
| Val | Asp | Leu | Asp | Arg | Leu | Asn | Asp | Asp | Ala | Lys | Arg | Tyr | Ser | Cys | Thr |      |
|     | 260 |     |     |     |     | 265 |     |     |     |     | 270 |     |     |     |     |      |
| ccc | agg | aat | tac | tcg | gtc | aat | ata | aga | gaa | gag | ctg | aag | ttg | gcc | aat | 1042 |
| Pro | Arg | Asn | Tyr | Ser | Val | Asn | Ile | Arg | Glu | Glu | Leu | Lys | Leu | Ala | Asn |      |
| 275 |     |     |     |     | 280 |     |     |     |     | 285 |     |     |     |     |     |      |
| gtg | gtc | ttc | ttt | cca | cgt | tgc | ctc | ctc | gtg | cag | cgc | tgt | gga | gga | aat | 1090 |
| Val | Val | Phe | Phe | Pro | Arg | Cys | Leu | Leu | Val | Gln | Arg | Cys | Gly | Gly | Asn |      |
| 290 |     |     |     |     | 295 |     |     |     |     | 300 |     |     |     |     | 305 |      |
| tgt | ggc | tgt | gga | act | gtc | aac | tgg | agg | tcc | tgc | aca | tgc | aat | tca | ggg | 1138 |
| Cys | Gly | Cys | Gly | Thr | Val | Asn | Trp | Arg | Ser | Cys | Thr | Cys | Asn | Ser | Gly |      |
|     |     |     |     | 310 |     |     |     |     | 315 |     |     |     |     | 320 |     |      |
| aaa | acc | gtg | aaa | aag | tat | cat | gag | gta | tta | cag | ttt | gag | cct | ggc | cac | 1186 |
| Lys | Thr | Val | Lys | Lys | Tyr | His | Glu | Val | Leu | Gln | Phe | Glu | Pro | Gly | His |      |
|     |     |     | 325 |     |     |     |     | 330 |     |     |     |     | 335 |     |     |      |
| atc | aag | agg | agg | ggt | aga | gct | aag | acc | atg | gct | cta | gtt | gac | atc | cag | 1234 |
| Ile | Lys | Arg | Arg | Gly | Arg | Ala | Lys | Thr | Met | Ala | Leu | Val | Asp | Ile | Gln |      |
|     | 340 |     |     |     |     | 345 |     |     |     |     | 350 |     |     |     |     |      |
| ttg | gat | cac | cat | gaa | cga | tgc | gat | tgt | atc | tgt | agc | tca | aga | cca | cct | 1282 |
| Leu | Asp | His | His | Glu | Arg | Cys | Asp | Cys | Ile | Cys | Ser | Ser | Arg | Pro | Pro |      |
| 355 |     |     |     |     |     | 360 |     |     |     |     | 365 |     |     |     |     |      |

| | |
|---|---|
| cga taagagaatg tgcacatcct tacattaagc ctgaaagaac ctttagttta | 1335 |
| Arg | |
| 370 | |
| aggagggtga gataagagac ccttttccta ccagcaacca aacttactac tagcctgcaa | 1395 |
| tgcaatgaac acaagtggtt gctgagtctc agccttgctt tgttaatgcc atggcaagta | 1455 |
| gaaaggtata tcatcaactt ctatacctaa gaatatagga ttgcatttaa taatagtgtt | 1515 |
| tgaggttata tatgcacaaa cacacacaga aatatattca tgtctatgtg tatatagatc | 1575 |
| aaatgttttt tttggtatat ataaccaggt acaccagagc ttacatatgt ttgagttaga | 1635 |
| ctcttaaaat cctttgccaa aataagggat ggtcaaatat atgaaacatg tctttagaaa | 1695 |
| atttaggaga taaatttatt tttaaatttt gaaacacaaa acaattttga atcttgctct | 1755 |
| cttaaagaaa gcatcttgta tattaaaaat caaaagatga ggctttctta catatacatc | 1815 |
| ttagttgatt attaaaaaag gaaaaaggtt tccagagaaa aggccaatac ctaagcattt | 1875 |
| tttccatgag aagcactgca tacttaccta tgtggactgt aataacctgt ctccaaaacc | 1935 |
| atgccataat aatataagtg ctttagaaat taaatcattg tgttttttat gcattttgct | 1995 |
| gaggcatcct tattcattta acacctatct caaaaactta cttagaaggt ttttattat | 2055 |
| agtcctacaa aagacaatgt ataagctgta acagaatttt gaattgtttt tctttgcaaa | 2115 |
| accccctccac aaaagcaaat cctttcaaga atggcatggg cattctgtat gaacctttcc | 2175 |
| agatggtgtt cagtgaaaga tgtgggtagt tgagaactta aaaagtgaac attgaaacat | 2235 |
| cgacgtaact ggaaaccg | 2253 |

<210> SEQ ID NO 2
<211> LENGTH: 370
<212> TYPE: PRT
<213> ORGANISM: Homo sapiens

<400> SEQUENCE: 2

```
Met His Arg Leu Ile Phe Val Tyr Thr Leu Ile Cys Ala Asn Phe Cys
 1               5                  10                  15

Ser Cys Arg Asp Thr Ser Ala Thr Pro Gln Ser Ala Ser Ile Lys Ala
            20                  25                  30

Leu Arg Asn Ala Asn Leu Arg Arg Asp Glu Ser Asn His Leu Thr Asp
        35                  40                  45

Leu Tyr Arg Arg Asp Glu Thr Ile Gln Val Lys Gly Asn Gly Tyr Val
    50                  55                  60

Gln Ser Pro Arg Phe Pro Asn Ser Tyr Pro Arg Asn Leu Leu Leu Thr
65                  70                  75                  80

Trp Arg Leu His Ser Gln Glu Asn Thr Arg Ile Gln Leu Val Phe Asp
                85                  90                  95

Asn Gln Phe Gly Leu Glu Glu Ala Glu Asn Asp Ile Cys Arg Tyr Asp
            100                 105                 110

Phe Val Glu Val Glu Asp Ile Ser Glu Thr Ser Thr Ile Ile Arg Gly
        115                 120                 125

Arg Trp Cys Gly His Lys Glu Val Pro Pro Arg Ile Lys Ser Arg Thr
    130                 135                 140

Asn Gln Ile Lys Ile Thr Phe Lys Ser Asp Asp Tyr Phe Val Ala Lys
145                 150                 155                 160

Pro Gly Phe Lys Ile Tyr Tyr Ser Leu Leu Glu Asp Phe Gln Pro Ala
                165                 170                 175

Ala Ala Ser Glu Thr Asn Trp Glu Ser Val Thr Ser Ser Ile Ser Gly
            180                 185                 190

Val Ser Tyr Asn Ser Pro Ser Val Thr Asp Pro Thr Leu Ile Ala Asp
        195                 200                 205

Ala Leu Asp Lys Lys Ile Ala Glu Phe Asp Thr Val Glu Asp Leu Leu
    210                 215                 220

Lys Tyr Phe Asn Pro Glu Ser Trp Gln Glu Asp Leu Glu Asn Met Tyr
225                 230                 235                 240

Leu Asp Thr Pro Arg Tyr Arg Gly Arg Ser Tyr His Asp Arg Lys Ser
                245                 250                 255

Lys Val Asp Leu Asp Arg Leu Asn Asp Asp Ala Lys Arg Tyr Ser Cys
            260                 265                 270

Thr Pro Arg Asn Tyr Ser Val Asn Ile Arg Glu Glu Leu Lys Leu Ala
        275                 280                 285

Asn Val Val Phe Phe Pro Arg Cys Leu Leu Val Gln Arg Cys Gly Gly
    290                 295                 300

Asn Cys Gly Cys Gly Thr Val Asn Trp Arg Ser Cys Thr Cys Asn Ser
305                 310                 315                 320

Gly Lys Thr Val Lys Lys Tyr His Glu Val Leu Gln Phe Glu Pro Gly
                325                 330                 335

His Ile Lys Arg Arg Gly Arg Ala Lys Thr Met Ala Leu Val Asp Ile
            340                 345                 350

Gln Leu Asp His His Glu Arg Cys Asp Cys Ile Cys Ser Ser Arg Pro
        355                 360                 365

Pro Arg
    370

<210> SEQ ID NO 3
<211> LENGTH: 200
<212> TYPE: PRT
<213> ORGANISM: Homo sapiens
```

<400> SEQUENCE: 3

```
Gly Arg Phe Pro Thr Arg Ser Ser Phe Arg Asp Gln Leu Glu Ser Val
  1               5                  10                  15

Thr Ser Ser Val Ser Gly Tyr Pro Tyr Asn Ser Pro Ser Val Thr Asp
             20                  25                  30

Pro Thr Leu Ile Ala Asp Ala Leu Asp Lys Lys Ile Ala Glu Phe Asp
         35                  40                  45

Thr Val Glu Asp Leu Leu Lys Tyr Phe Asn Pro Glu Ser Trp Gln Glu
     50                  55                  60

Asp Leu Glu Asn Met Tyr Leu Asp Thr Pro Arg Tyr Arg Gly Arg Ser
 65                  70                  75                  80

Tyr His Asp Arg Lys Ser Lys Val Asp Leu Asp Arg Leu Asn Asp Asp
                 85                  90                  95

Ala Lys Arg Tyr Ser Cys Thr Pro Arg Asn Tyr Ser Val Asn Ile Arg
             100                 105                 110

Glu Glu Leu Lys Leu Ala Asn Val Val Phe Phe Pro Arg Cys Leu Leu
         115                 120                 125

Val Gln Arg Cys Gly Gly Asn Cys Gly Cys Gly Thr Val Lys Leu Glu
     130                 135                 140

Ser Cys Thr Cys Asn Ser Gly Lys Thr Val Lys Lys Tyr His Glu Val
145                 150                 155                 160

Leu Gln Phe Glu Pro Gly His Ile Lys Arg Arg Gly Arg Ala Lys Thr
                 165                 170                 175

Met Ala Leu Val Asp Ile Gln Leu Asp His His Glu Arg Cys Asp Cys
             180                 185                 190

Ile Cys Ser Ser Arg Pro Pro Arg
             195                 200
```

<210> SEQ ID NO 4
<211> LENGTH: 322
<212> TYPE: PRT
<213> ORGANISM: Homo sapiens

<400> SEQUENCE: 4

```
Leu Tyr Arg Arg Asp Glu Thr Ile Gln Val Lys Gly Asn Gly Tyr Val
  1               5                  10                  15

Gln Ser Pro Arg Phe Pro Asn Ser Tyr Pro Arg Asn Leu Leu Leu Thr
             20                  25                  30

Trp Arg Leu His Ser Gln Glu Asn Thr Arg Ile Gln Leu Val Phe Asp
         35                  40                  45

Asn Gln Phe Gly Leu Glu Glu Ala Glu Asn Asp Ile Cys Arg Tyr Asp
     50                  55                  60

Phe Val Glu Val Glu Asp Ile Ser Glu Thr Ser Thr Ile Ile Arg Gly
 65                  70                  75                  80

Arg Trp Cys Gly His Lys Glu Val Pro Pro Arg Ile Lys Ser Arg Thr
                 85                  90                  95

Asn Gln Ile Lys Ile Thr Phe Lys Ser Asp Asp Tyr Phe Val Ala Lys
             100                 105                 110

Pro Gly Phe Lys Ile Tyr Tyr Ser Leu Leu Glu Asp Phe Gln Pro Ala
         115                 120                 125

Ala Ala Ser Glu Thr Asn Trp Glu Ser Val Thr Ser Ser Ile Ser Gly
     130                 135                 140

Val Ser Tyr Asn Ser Pro Ser Val Thr Asp Pro Thr Leu Ile Ala Asp
145                 150                 155                 160
```

```
Ala Leu Asp Lys Lys Ile Ala Glu Phe Asp Thr Val Glu Asp Leu Leu
            165                 170                 175

Lys Tyr Phe Asn Pro Glu Ser Trp Gln Glu Asp Leu Glu Asn Met Tyr
            180                 185                 190

Leu Asp Thr Pro Arg Tyr Arg Gly Arg Ser Tyr His Asp Arg Lys Ser
            195                 200                 205

Lys Val Asp Leu Asp Arg Leu Asn Asp Asp Ala Lys Arg Tyr Ser Cys
            210                 215                 220

Thr Pro Arg Asn Tyr Ser Val Asn Ile Arg Glu Glu Leu Lys Leu Ala
225                 230                 235                 240

Asn Val Val Phe Phe Pro Arg Cys Leu Leu Val Gln Arg Cys Gly Gly
                    245                 250                 255

Asn Cys Gly Cys Gly Thr Val Asn Trp Arg Ser Cys Thr Cys Asn Ser
            260                 265                 270

Gly Lys Thr Val Lys Lys Tyr His Glu Val Leu Gln Phe Glu Pro Gly
            275                 280                 285

His Ile Lys Arg Arg Gly Arg Ala Lys Thr Met Ala Leu Val Asp Ile
            290                 295                 300

Gln Leu Asp His His Glu Arg Cys Asp Cys Ile Cys Ser Ser Arg Pro
305                 310                 315                 320

Pro Arg

<210> SEQ ID NO 5
<211> LENGTH: 8
<212> TYPE: PRT
<213> ORGANISM: Homo sapiens

<400> SEQUENCE: 5

Ile Glu Gly Arg Ile Glu Gly Arg
  1               5

<210> SEQ ID NO 6
<211> LENGTH: 345
<212> TYPE: PRT
<213> ORGANISM: Homo sapiens

<400> SEQUENCE: 6

Met Ser Leu Phe Gly Leu Leu Leu Val Thr Ser Ala Leu Ala Gly Gln
  1               5                  10                  15

Arg Arg Gly Thr Gln Ala Glu Ser Asn Leu Ser Ser Lys Phe Gln Phe
             20                  25                  30

Ser Ser Asn Lys Glu Gln Asn Gly Val Gln Asp Pro Gln His Glu Arg
             35                  40                  45

Ile Ile Thr Val Ser Thr Asn Gly Ser Ile His Ser Pro Arg Phe Pro
         50                  55                  60

His Thr Tyr Pro Arg Asn Thr Val Leu Val Trp Arg Leu Val Ala Val
 65                  70                  75                  80

Glu Glu Asn Val Trp Ile Gln Leu Thr Phe Asp Glu Arg Phe Gly Leu
                 85                  90                  95

Glu Asp Pro Glu Asp Asp Ile Cys Lys Tyr Asp Phe Val Glu Val Glu
            100                 105                 110

Glu Pro Ser Asp Gly Thr Ile Leu Gly Arg Trp Cys Gly Ser Gly Thr
            115                 120                 125

Val Pro Gly Lys Gln Ile Ser Lys Gly Asn Gln Ile Arg Ile Arg Phe
            130                 135                 140

Val Ser Asp Glu Tyr Phe Pro Ser Glu Pro Gly Phe Cys Ile His Tyr
```

```
                145                 150                 155                 160
Asn Ile Val Met Pro Gln Phe Thr Glu Ala Val Ser Pro Ser Val Leu
                165                 170                 175
Pro Pro Ser Ala Leu Pro Leu Asp Leu Leu Asn Asn Ala Ile Thr Ala
                180                 185                 190
Phe Ser Thr Leu Glu Asp Leu Ile Arg Tyr Leu Glu Pro Glu Arg Trp
                195                 200                 205
Gln Leu Asp Leu Glu Asp Leu Tyr Arg Pro Thr Trp Gln Leu Leu Gly
                210                 215                 220
Lys Ala Phe Val Phe Gly Arg Lys Ser Arg Val Val Asp Leu Asn Leu
225                 230                 235                 240
Leu Thr Glu Glu Val Arg Leu Tyr Ser Cys Thr Pro Arg Asn Phe Ser
                245                 250                 255
Val Ser Ile Arg Glu Glu Leu Lys Arg Thr Asp Thr Ile Phe Trp Pro
                260                 265                 270
Gly Cys Leu Leu Val Lys Arg Cys Gly Asn Cys Ala Cys Cys Leu
                275                 280                 285
His Asn Cys Asn Glu Cys Gln Cys Val Pro Ser Lys Val Thr Lys Lys
                290                 295                 300
Tyr His Glu Val Leu Gln Leu Arg Pro Lys Thr Gly Val Arg Gly Leu
305                 310                 315                 320
His Lys Ser Leu Thr Asp Val Ala Leu Glu His His Glu Glu Cys Asp
                325                 330                 335
Cys Val Cys Arg Gly Ser Thr Gly Gly
                340                 345

<210> SEQ ID NO 7
<211> LENGTH: 118
<212> TYPE: PRT
<213> ORGANISM: Homo sapiens

<400> SEQUENCE: 7

Asp Glu Thr Ile Gln Val Lys Gly Asn Gly Tyr Val Gln Ser Pro Arg
1               5                   10                  15
Phe Pro Asn Ser Tyr Pro Arg Asn Leu Leu Leu Thr Trp Arg Leu His
                20                  25                  30
Ser Gln Glu Asn Thr Arg Ile Gln Leu Val Phe Asp Asn Gln Phe Gly
                35                  40                  45
Leu Glu Glu Ala Glu Asn Asp Ile Cys Arg Tyr Asp Phe Val Glu Val
        50                  55                  60
Glu Asp Ile Ser Glu Thr Ser Thr Ile Ile Arg Gly Arg Trp Cys Gly
65                  70                  75                  80
His Lys Glu Val Pro Pro Arg Ile Lys Ser Arg Thr Asn Gln Ile Lys
                85                  90                  95
Ile Thr Phe Lys Ser Asp Asp Tyr Phe Val Ala Lys Pro Gly Phe Lys
                100                 105                 110
Ile Tyr Tyr Ser Leu Leu
        115

<210> SEQ ID NO 8
<211> LENGTH: 113
<212> TYPE: PRT
<213> ORGANISM: Homo sapiens

<400> SEQUENCE: 8

Cys Gly Glu Thr Leu Gln Asp Ser Thr Gly Asn Phe Ser Ser Pro Glu
```

```
                1               5                   10                  15
Tyr Pro Asn Gly Tyr Ser Ala His Met His Cys Val Trp Arg Ile Ser
                20                  25                  30

Val Thr Pro Gly Glu Lys Ile Ile Leu Asn Phe Thr Ser Leu Asp Leu
                35                  40                  45

Tyr Arg Ser Arg Leu Cys Trp Tyr Asp Tyr Val Glu Val Arg Asp Gly
                50                  55                  60

Phe Trp Arg Lys Ala Pro Leu Arg Gly Arg Phe Cys Gly Ser Lys Leu
 65                 70                  75                  80

Pro Glu Pro Ile Val Ser Thr Asp Ser Arg Leu Trp Val Glu Phe Arg
                85                  90                  95

Ser Ser Ser Asn Trp Val Gly Lys Gly Phe Phe Ala Val Tyr Glu Ala
                100                 105                 110

Ile

<210> SEQ ID NO 9
<211> LENGTH: 112
<212> TYPE: PRT
<213> ORGANISM: Homo sapiens

<400> SEQUENCE: 9

Cys Gly Gly Asp Val Lys Lys Asp Tyr Gly His Ile Gln Ser Pro Asn
 1               5                   10                  15

Tyr Pro Asp Asp Tyr Arg Pro Ser Lys Val Cys Ile Trp Arg Ile Gln
                20                  25                  30

Val Ser Glu Gly Phe His Val Gly Leu Thr Phe Gln Ser Phe Glu Ile
                35                  40                  45

Glu Arg Met Asp Ser Cys Ala Tyr Asp Tyr Leu Glu Val Arg Asp Gly
                50                  55                  60

His Ser Glu Ser Ser Thr Leu Ile Gly Arg Tyr Cys Gly Tyr Glu Lys
 65                 70                  75                  80

Pro Asp Asp Ile Lys Ser Thr Ser Ser Arg Leu Trp Leu Lys Phe Val
                85                  90                  95

Ser Asp Gly Ser Ile Asn Lys Ala Gly Phe Ala Val Asn Phe Phe Lys
                100                 105                 110

<210> SEQ ID NO 10
<211> LENGTH: 113
<212> TYPE: PRT
<213> ORGANISM: Homo sapiens

<400> SEQUENCE: 10

Cys Gly Gly Phe Leu Thr Lys Leu Asn Gly Ser Ile Thr Ser Pro Gly
 1               5                   10                  15

Trp Pro Lys Glu Tyr Pro Pro Asn Lys Asn Cys Ile Trp Gln Leu Val
                20                  25                  30

Ala Pro Thr Gln Tyr Arg Ile Ser Leu Gln Phe Asp Phe Phe Glu Thr
                35                  40                  45

Glu Gly Asn Asp Val Cys Lys Tyr Asp Phe Val Glu Val Arg Ser Gly
                50                  55                  60

Leu Thr Ala Asp Ser Lys Leu His Gly Lys Phe Cys Gly Ser Glu Lys
 65                 70                  75                  80

Pro Glu Val Ile Thr Ser Gln Tyr Asn Asn Met Arg Val Glu Pro Lys
                85                  90                  95

Ser Asp Asn Thr Val Ser Lys Lys Gly Phe Lys Ala His Phe Phe Ser
                100                 105                 110
```

Glu

<210> SEQ ID NO 11
<211> LENGTH: 113
<212> TYPE: PRT
<213> ORGANISM: Homo sapiens

<400> SEQUENCE: 11

Gly Asp Thr Ile Lys Ile Glu Ser Pro Gly Tyr Leu Thr Ser Pro Gly
 1               5                  10                  15

Tyr Pro His Ser Tyr His Pro Ser Glu Lys Cys Glu Trp Leu Ile Gln
                20                  25                  30

Ala Pro Asp Pro Tyr Gln Arg Ile Met Ile Asn Phe Asn Pro His Phe
            35                  40                  45

Asp Leu Glu Asp Arg Asp Cys Lys Tyr Asp Tyr Val Glu Val Phe Asp
        50                  55                  60

Gly Glu Asn Glu Asn Gly His Phe Arg Gly Lys Phe Cys Gly Lys Ile
 65                  70                  75                  80

Ala Pro Pro Pro Val Val Ser Ser Gly Pro Phe Leu Phe Ile Lys Phe
                85                  90                  95

Val Ser Asp Tyr Glu Thr His Gly Ala Gly Phe Ser Ile Arg Tyr Glu
            100                 105                 110

Ile

<210> SEQ ID NO 12
<211> LENGTH: 119
<212> TYPE: PRT
<213> ORGANISM: Homo sapiens

<400> SEQUENCE: 12

Cys Ser Gln Asn Tyr Thr Thr Pro Ser Gly Val Ile Lys Ser Pro Gly
 1               5                  10                  15

Phe Pro Glu Lys Tyr Pro Asn Ser Leu Glu Cys Thr Tyr Ile Val Phe
                20                  25                  30

Ala Pro Lys Met Ser Glu Ile Ile Leu Glu Phe Glu Ser Phe Asp Leu
            35                  40                  45

Glu Pro Asp Ser Asn Pro Pro Gly Gly Met Phe Cys Arg Tyr Asp Arg
        50                  55                  60

Leu Glu Ile Trp Asp Gly Phe Pro Asp Val Gly Pro His Ile Gly Arg
 65                  70                  75                  80

Tyr Cys Gly Gln Lys Thr Pro Gly Arg Ile Arg Ser Ser Ser Gly Ile
                85                  90                  95

Leu Ser Met Val Phe Tyr Thr Asp Ser Ala Ile Ala Lys Glu Gly Phe
            100                 105                 110

Ser Ala Asn Tyr Ser Val Leu
        115

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gcggatcctt gcctagtgtt tctcttgatc                                        30

```
<210> SEQ ID NO 14
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ccagtcacct gctccggatc ttcatggacc ctgacaaatg                            40

<210> SEQ ID NO 15
<211> LENGTH: 132
<212> TYPE: PRT
<213> ORGANISM: Orf virus

<400> SEQUENCE: 15

Met Lys Phe Leu Val Gly Ile Leu Val Ala Val Cys Leu His Gln Tyr
 1               5                  10                  15

Leu Leu Asn Ala Asp Ser Thr Lys Thr Trp Ser Glu Val Phe Glu Asn
                20                  25                  30

Ser Gly Cys Lys Pro Arg Pro Met Val Phe Arg Val His Asp Glu His
            35                  40                  45

Pro Glu Leu Thr Ser Gln Arg Phe Asn Pro Pro Cys Val Thr Leu Met
    50                  55                  60

Arg Cys Gly Gly Cys Cys Asn Asp Glu Ser Leu Glu Cys Val Pro Thr
65                  70                  75                  80

Glu Glu Ala Asn Val Thr Met Gln Leu Met Gly Ala Ser Val Ser Gly
                85                  90                  95

Gly Asn Gly Met Gln His Leu Ser Phe Val Glu His Lys Lys Cys Asp
            100                 105                 110

Cys Lys Pro Pro Leu Thr Thr Thr Pro Pro Thr Thr Thr Arg Pro Pro
        115                 120                 125

Arg Arg Arg Arg
    130

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 16

His His His His His His
 1               5
```